(12) United States Patent
Kikitsu et al.

(10) Patent No.: US 11,703,530 B2
(45) Date of Patent: Jul. 18, 2023

(54) SENSOR AND INSPECTION DEVICE

(71) Applicant: KABUSHIKI KAISHA TOSHIBA, Tokyo (JP)

(72) Inventors: Akira Kikitsu, Yokohama Kanagawa (JP); Satoshi Shirotori, Yokohama Kanagawa (JP); Yoshihiro Higashi, Komatsu Ishikawa (JP); Yoshinari Kurosaki, Kawasaki Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 17/672,097

(22) Filed: Feb. 15, 2022

(65) Prior Publication Data

US 2023/0041879 A1 Feb. 9, 2023

(30) Foreign Application Priority Data

Aug. 6, 2021 (JP) ................. 2021-129777

(51) Int. Cl.
*G01R 27/02* (2006.01)
*G01R 25/00* (2006.01)
*G01R 31/382* (2019.01)
*G01R 17/10* (2006.01)
(Continued)

(52) U.S. Cl.
CPC .............. *G01R 27/02* (2013.01); *G01R 25/00* (2013.01); *G01R 31/382* (2019.01);
(Continued)

(58) Field of Classification Search
CPC ........ G01R 27/00; G01R 27/02; G01R 27/08; G01R 27/14; G01R 25/00; G01R 31/00;
(Continued)

(56) References Cited

U.S. PATENT DOCUMENTS 11,237,230 B1 * 2/2022 Iwasaki ................ A61B 5/6803
11,402,441 B2 * 8/2022 Kikitsu ............. G01R 33/0011
(Continued)

FOREIGN PATENT DOCUMENTS

| JP | 2009122240 A | * | 6/2009 | ............ G01R 33/12 |
| JP | 2016114408 A | * | 6/2016 | ............ G01R 33/09 |

(Continued)

*Primary Examiner* — Hoai-An D. Nguyen
(74) *Attorney, Agent, or Firm* — Finnegan, Henderson, Farabow, Garrett & Dunner, LLP

(57) ABSTRACT

According to one embodiment, a sensor includes an element part, and a control circuit part. The element part includes first and second elements. Each of the first and second elements includes a first magnetic element and a first conductive member. The control circuit part includes a first current circuit, a differential circuit, and a phase detection circuit. The first current circuit is configured to supply a first current to the first conductive member. The differential circuit is configured to output a differential signal corresponding to a difference of a first signal and a second signal. The first signal corresponds to a change in a first electrical resistance of the first magnetic element of the first element. The second signal corresponds to a change in a second electrical resistance of the first magnetic element of the second element. The phase detection circuit is configured to perform a phase detection of the differential signal.

20 Claims, 15 Drawing Sheets

(51) Int. Cl.
  *G01R 27/08* (2006.01)
  *G01R 27/14* (2006.01)
(52) U.S. Cl.
  CPC ............ *G01R 17/105* (2013.01); *G01R 27/08* (2013.01); *G01R 27/14* (2013.01)
(58) Field of Classification Search
  CPC ...... G01R 31/36; G01R 31/382; G01R 17/00; G01R 17/10; G01R 17/105; G01R 19/00; G01R 19/0084; G01R 19/0092
  USPC ............ 324/600, 649, 691, 704, 709, 76.11, 324/76.77
  See application file for complete search history.

(56) References Cited

U.S. PATENT DOCUMENTS

| | | | |
|---|---|---|---|
| 11,432,751 B2* | 9/2022 | Shirotori | G01R 33/09 |
| 11,493,571 B2* | 11/2022 | Iwasaki | G01R 33/0029 |
| 11,493,572 B2* | 11/2022 | Higashi | G01R 33/098 |
| 2017/0363606 A1 | 12/2017 | Kikitsu et al. | |
| 2018/0271395 A1 | 9/2018 | Iwasaki et al. | |
| 2019/0369172 A1 | 12/2019 | Kikitsu et al. | |
| 2022/0187247 A1* | 6/2022 | Iwasaki | H01M 10/48 |
| 2022/0214401 A1* | 7/2022 | Iwasaki | G01R 33/0011 |
| 2022/0283249 A1* | 9/2022 | Iwasaki | G01R 33/093 |

FOREIGN PATENT DOCUMENTS

| | | |
|---|---|---|
| JP | 2018-155719 A | 10/2018 |
| JP | 2019-207167 A | 12/2019 |
| JP | 6668176 B2 | 3/2020 |

\* cited by examiner

Hsig=0

+Hsig

-Hsig

SENSOR AND INSPECTION DEVICE

CROSS-REFERENCE TO RELATED APPLICATIONS

This application is based upon and claims the benefit of priority from Japanese Patent Application No. 2021-129777, filed on Aug. 6, 2021; the entire contents of which are incorporated herein by reference.

FIELD

Embodiments described herein relate generally to a sensor and an inspection device.

BACKGROUND

There is a sensor that uses a magnetic layer. There is an inspection device that uses a sensor. It is desired to improve the characteristics of the sensor.

BRIEF DESCRIPTION OF THE DRAWINGS

FIGS. 2A and 26 are schematic views illustrating characteristics of the sensor according to the first embodiment;

FIGS. 3A and 36 are schematic views illustrating characteristics of the sensor according to the first embodiment;

FIGS. 6A and 66 are schematic views illustrating characteristics of the sensors;

DETAILED DESCRIPTION

Figure 1:
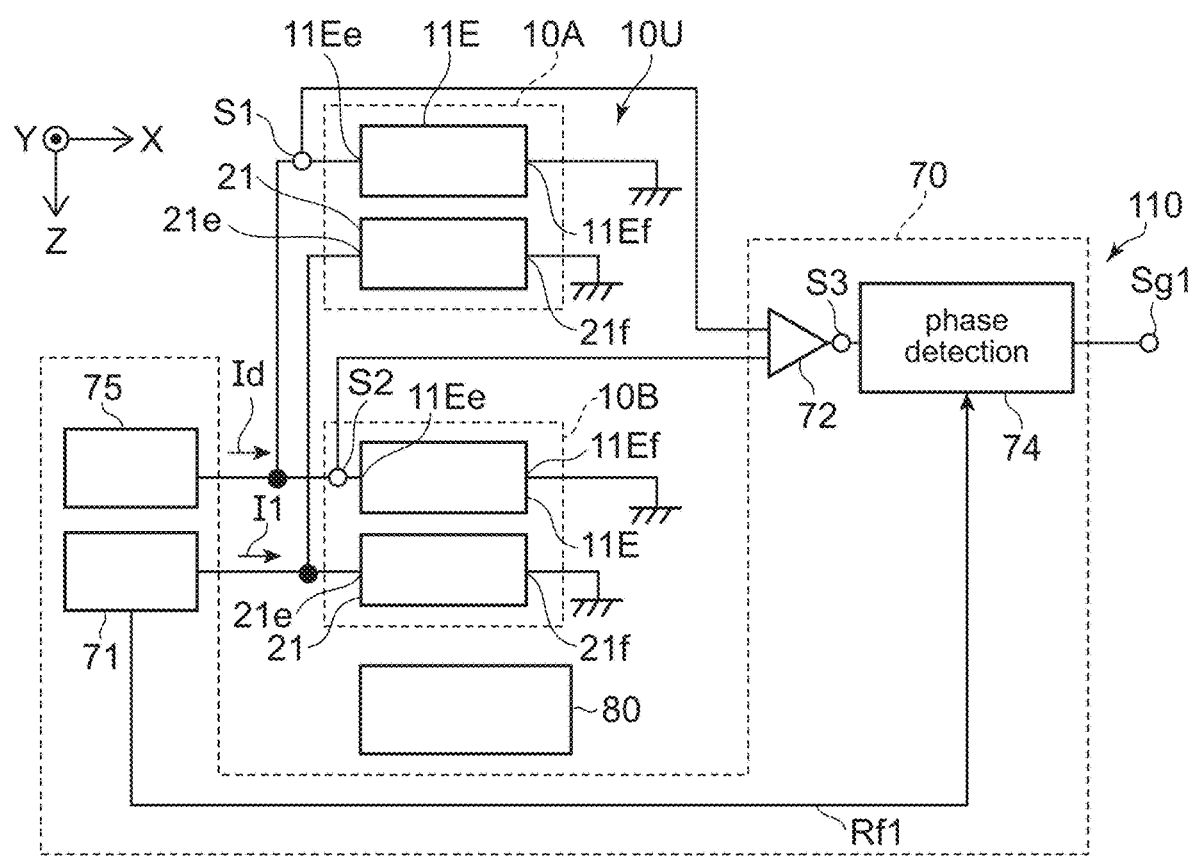
FIG. 1 is a schematic view illustrating a sensor according to a first embodiment.

According to one embodiment, a sensor includes an element part, and a control circuit part. The element part includes a first element and a second element. Each of the first element and the second element includes a first magnetic element and a first conductive member. The control circuit part includes a first current circuit, a differential circuit, and a phase detection circuit. The first current circuit is configured to supply a first current to the first conductive member. The first current includes an AC component. The differential circuit is configured to output a differential signal corresponding to a difference of a first signal and a second signal. The first signal corresponds to a change in a first electrical resistance of the first magnetic dement of the first element. The second signal corresponds to a change in a second electrical resistance of the first magnetic dement of the second element. The phase detection circuit is configured to perform a phase-detection of the differential signal with reference to the AC component. The first electrical resistance changes in an even function with respect to the first current. The second electrical resistance changes in an even function with respect to the first current.

According to one embodiment, an inspection device includes the sensor described above, and a processor configured to process a signal from the sensor.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic view illustrating a sensor according to a first embodiment.

As shown in FIG. 1, a sensor 110 according to the embodiment includes an element part 10U and a control circuit part 70. The element part 10U includes a first element 10A and a second element 10B. Each of the first element 10A and the second element 10B includes a first magnetic element 11E and a first conductive member 21.

The control circuit part 70 includes a first current circuit 71, a differential circuit 72, and a phase detection circuit 74, The first current circuit 71 is configured to supply a first current I1 to the first conductive member 21 of each of the first element 10A and the second element 10B. The first current I1 includes an AC component. The first current I1 is, for example, an alternating current.

From the first magnetic element 11E of the first element 10A, a first signal S1 corresponding to a change in a first electrical resistance of the first magnetic element 11E of the first element 10A is obtained. From the first magnetic element 11E of the second element 10B, a second signal S2 corresponding to a change in a second electrical resistance of the first magnetic element 11E of the second element 10B is obtained.

The first signal S1 and the second signal S2 are supplied to the differential circuit 72. The differential circuit 72 is configured to output a differential signal S3. The differential signal S3 corresponds to a difference between the first signal S1 corresponding to the change in the first electrical resistance of the first magnetic element 11E of the first element 10A and the second signal corresponding to the change in the second electrical resistance of the first magnetic element 11E of the second element 10B.

The phase detection circuit 74 performs the phase-detection of the difference signal S3 with reference to an AC component. In this example, a reference signal Rf1 corresponding to the AC component of the first current I1 is supplied from the first current circuit 71 to the phase detection circuit 74. The difference signal S3 is supplied to the phase detection circuit 74. The phase detection circuit 74 demodulates the difference signal S3 based on the reference signal Rf1 and outputs an output signal Sg1.

The first electrical resistance changes in an even function with respect to the first current I1. The second electrical resistance changes in an even function with respect to the first current I1. The first magnetic element 11E of the first element 10A and the first magnetic element 11E of the second element 10B are, for example, even function elements. The first current I1 including an AC component is supplied to the first conductive member 21 combined with the first magnetic element 11E. As a result, a magnetic field from a detection object 80 can be detected with higher accuracy.

As shown in FIG. 1, for example, the control circuit part 70 may further include an element current circuit 75. The element current circuit 75 is configured to supply an element current Id to the first magnetic element 11E of each of the first element 10A and the second element 10B. Using the element current Id, the first signal S1 corresponding to the change in the first electrical resistance of the first magnetic element 11E of the first element 10A can be obtained from the first element 10A. Using the element current Id, the second signal S2 corresponding to the change in the second electrical resistance of the first magnetic element 11E of the second element 10B can be obtained from the second element 10B.

For example, the first signal S1 is generated at a connection point between the element current circuit 75 and the first magnetic element 11E of the first element 10A. For example, the second signal S2 is generated at a connection point between the element current circuit 75 and the first magnetic element 11E of the second element 10B. The other part of the first magnetic element 11E of the first element 10A and the other part of the first magnetic element 11E of the second element 10B are set to, for example, the ground potential.

FIG. 1 illustrates the element part 10U. In each of the first element 10A and the second element 10B, the first magnetic element 11E includes one end part 11Ee and other end part 11Ef. The element current Id flows from the one end part 11Ee to the other end part 11Ef. In each of the first element 10A and the second element 10B, the first conductive member 21 includes a first conductive member one part 21e and a first conductive member other part 21f. The first conductive member one part 21e corresponds to the one end part 11Ee of the first magnetic element 11E. The first conductive member other part 21f corresponds to the other end part 11Ef of the first magnetic element 11E.

For example, a first direction from the one end part 11Ee to the other end part 11Ef is defined as an X-axis direction. A direction perpendicular to the X-axis direction is defined as a Y-axis direction. A direction perpendicular to the X-axis direction and the Y-axis direction is defined as a Z-axis direction.

The first current I1 has an orientation from the first conductive member one part 21e to the first conductive member other part 21f, or an orientation from the first conductive member other part 21f to the first conductive member one part 21e. The first current I1 includes a component along the X-axis direction. The first conductive member 21 and the first magnetic element 11E having such a configuration are combined. In the first magnetic element 11E, an even function-like change in electrical resistance is obtained with respect to the first current I1.

Hereinafter, an example of the change in the electrical resistance of the first magnetic element 11E when the first current I1 flows through the first conductive member 21 will be described. The following description can be applied to the second to fourth magnetic elements described later.

Figure 2A:
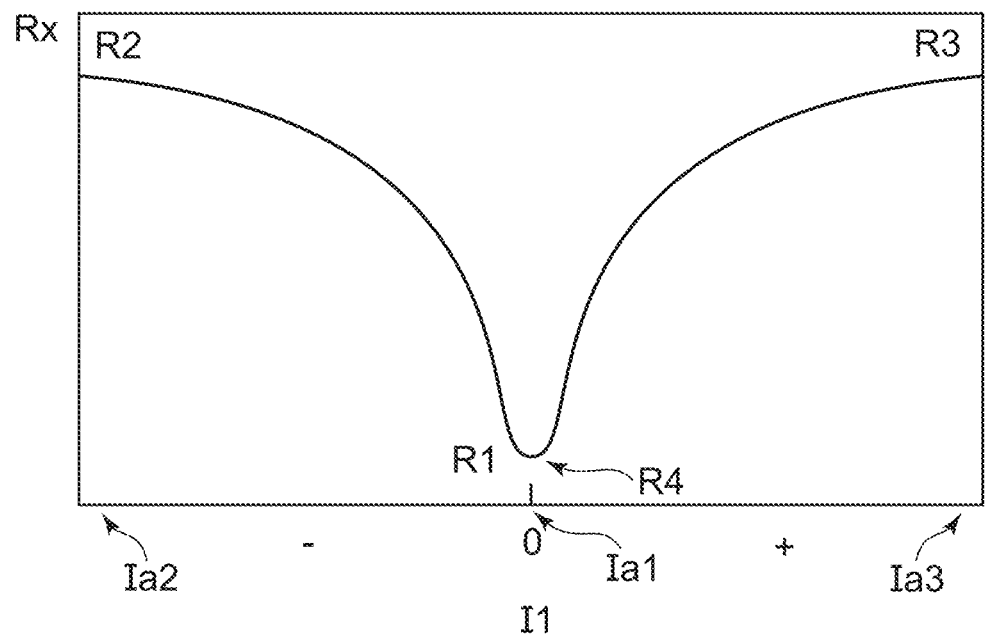
Figure 2B:
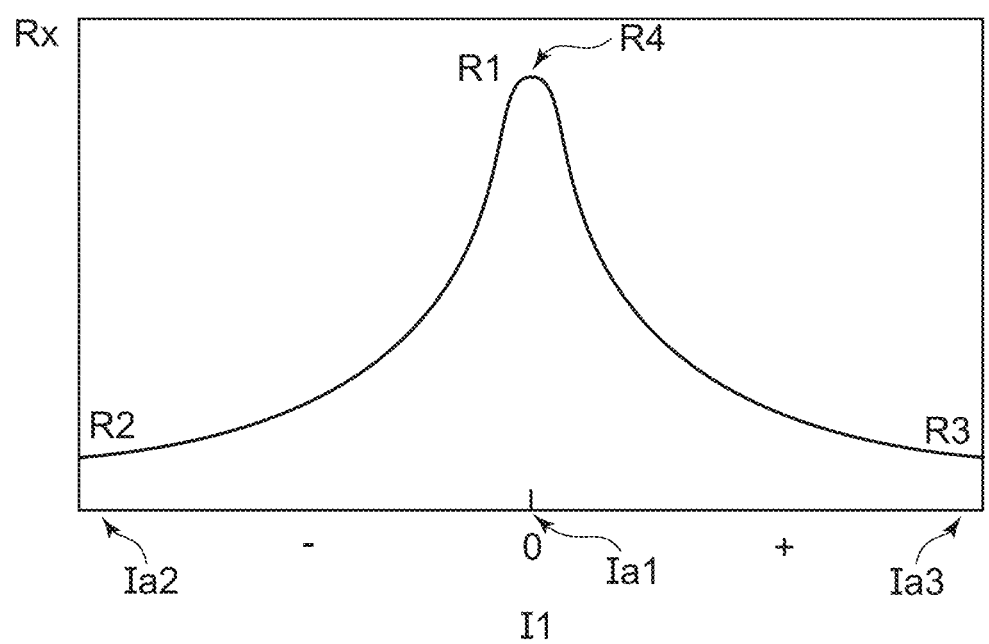

FIGS. 2A and 2B are schematic views illustrating characteristics of the sensor according to the first embodiment.

The horizontal axis of these figures corresponds to a value of the first current I1 flowing through the first conductive member 21. The vertical axis is an electrical resistance Rx of the first magnetic element 11E. As shown in FIGS. 2A and 2B, in the embodiment, the electrical resistance Rx shows the characteristic of an even function with respect to the change of the first current I1.

For example, the electrical resistance Rx of the first magnetic element 11E has a first value R1 when a first value current Ia1 is supplied to the first conductive member 21. The electrical resistance Rx has a second value R2 when a second value current Ia2 is supplied to the first conductive member 21. The electrical resistance Rx has a third value R3 when a third value current Ia3 is supplied to the first conductive member 21. The absolute value of the first value current Ia1 is smaller than the absolute value of the second value current Ia2 and smaller than the absolute value of the third value current Ia3. The first value current Ia1 may be, for example, substantially 0. The orientation of the second value current Ia2 is opposite to the orientation of the third value current Ia3.

In the example of FIG. 2A, the first value R1 is lower than the second value R2 and lower than the third value R3. The first value R1 is, for example, the lowest value of electrical resistance. In the example of FIG. 2B, the first value R1 is higher than the second value R2 and higher than the third value R3. The first value R1 is, for example, the highest value of electrical resistance.

For example, when no current flows through the first conductive member 21, the electrical resistance Rx has a fourth value R4. For example, the first value R1 may be substantially the same as the fourth value R4 when no current flows. For example, a ratio of the absolute value of the difference between the first value R1 and the fourth value R4 to the fourth value R4 is not more than 0.01. The ratio may be not more than 0.001. For positive and negative currents, the characteristics of an even function can be obtained.

Such a relationship between the first current I1 and the electrical resistance Rx is based on that the magnetic field due to the first current I1 is applied to the first magnetic element 11E, and the electrical resistance Rx of the first magnetic element 11E changes depending on the strength of the magnetic field.

The electrical resistance Rx when an external magnetic field is applied to the first magnetic element 11E also shows the characteristics of an even function as in the example shown in FIG. 2A or 2B. The external magnetic field includes, for example, components along the Z-axis direction.

Figure 3A:
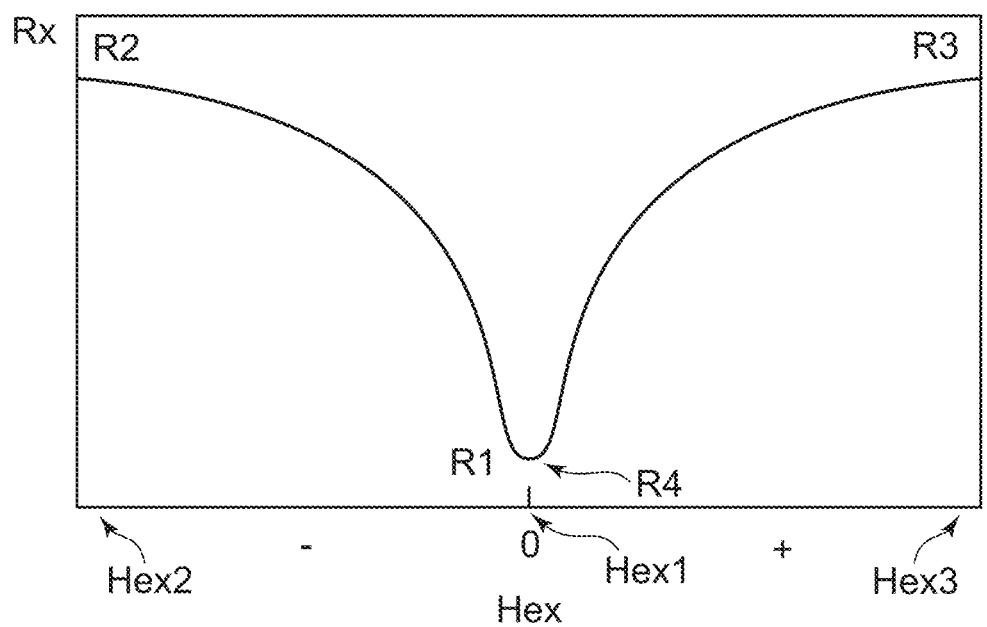
Figure 3B:
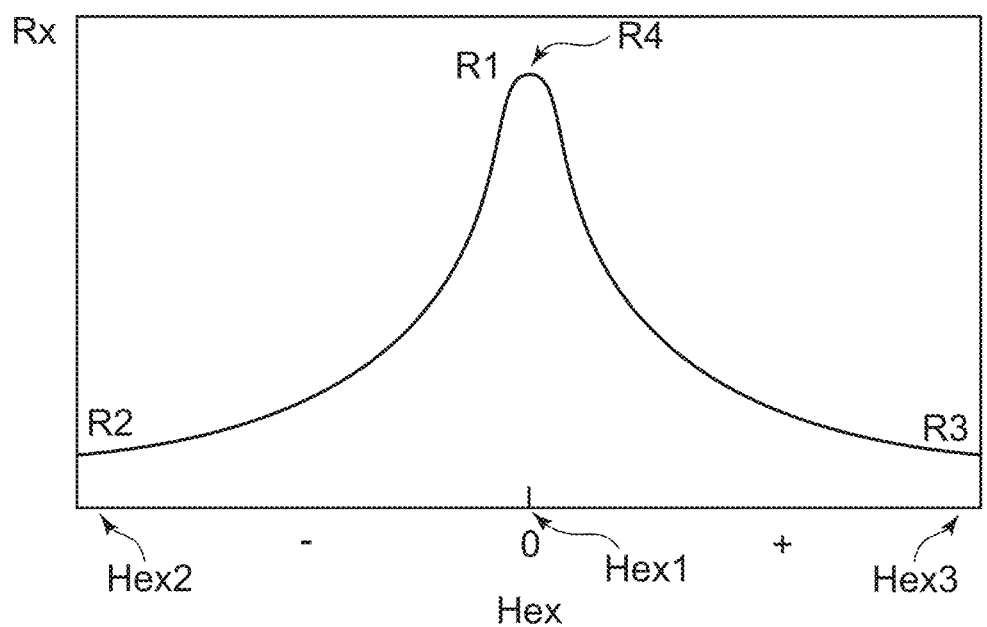

FIGS. 3A and 3B are schematic views illustrating characteristics of the sensor according to the first embodiment.

The horizontal axis of these figures is the strength of the external magnetic field Hex applied to the first magnetic element 11E. The vertical axis is the electrical resistance Rx of the first magnetic element 11E. These figures correspond to the R-H characteristics. As shown in FIGS. 3A and 3B, the electrical resistance Rx has the property of even function with respect to the magnetic field applied to the first magnetic element 11E (external magnetic field Hex, for example, the magnetic field including a component in the Z-axis direction).

As shown in FIGS. 3A and 3B, the electrical resistance Rx of the first magnetic element 11E has the first value R1 when a first magnetic field Hex1 is applied to the first magnetic element 11E. The electrical resistance Rx has the second value R2 when a second magnetic field Hex2 is applied to the first magnetic element 11E. The electric resistance Rx has the third value R3 when a third magnetic field Hex3 is applied to the first magnetic element 11E. The absolute value of the first magnetic field Hex1 is smaller than the absolute value of the second magnetic field Hex2 and smaller than the absolute value of the third magnetic field Hex3. The orientation of the second magnetic field Hex2 is opposite to the orientation of the third magnetic field Hex3.

In the example of FIG. 3A, the first value R1 is lower than the second value R2 and lower than the third value R3. In the example of FIG. 3B, the first value R1 is higher than the second value R2 and higher than the third value R3. For example, when the external magnetic field Hex is not applied to the first magnetic element 11E, the electrical resistance Rx has a fourth value R4. The first value R1 is substantially the same as the fourth value R4 when the external magnetic field Hex is not applied. For example, the ratio of the absolute value of the difference between the first value R1 and the fourth value R4 to the fourth value R4 is not more than 0.01. The ratio may be not more than 0.001. The characteristics of an even function can be obtained with respect to positive and negative external magnetic fields.

Utilizing such characteristics of even functions, high-sensitivity detection is possible as follows.

In the following, an example will be described in which the first current I1 is an alternating current and does not substantially include a DC component. A first current I1 (alternating current) is supplied to the first conductive member 21, and an alternating magnetic field generated by the alternating current is applied to the first magnetic element 11E. An example of the change in the electrical resistance Rx at this time will be described.

Figure 4A:
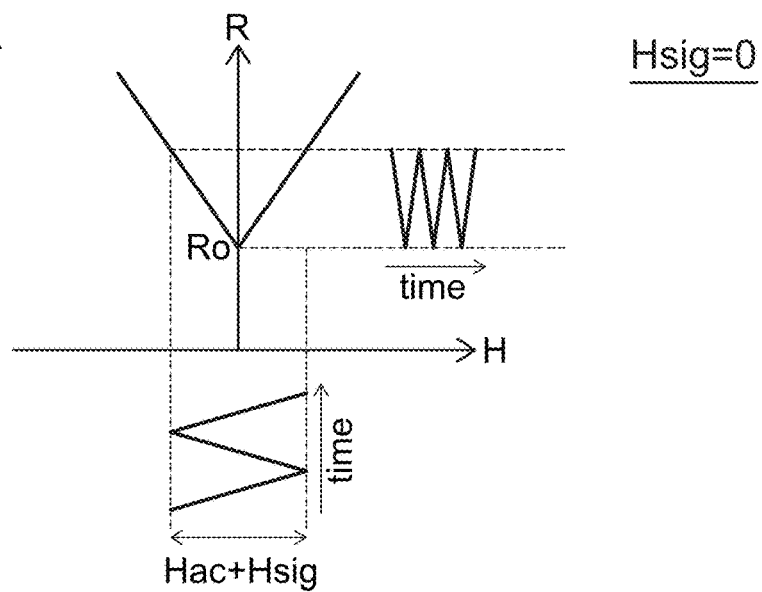
FIGS. 4A to 4C are graphs illustrating characteristics of the sensor according to the first embodiment.
Figure 4B:
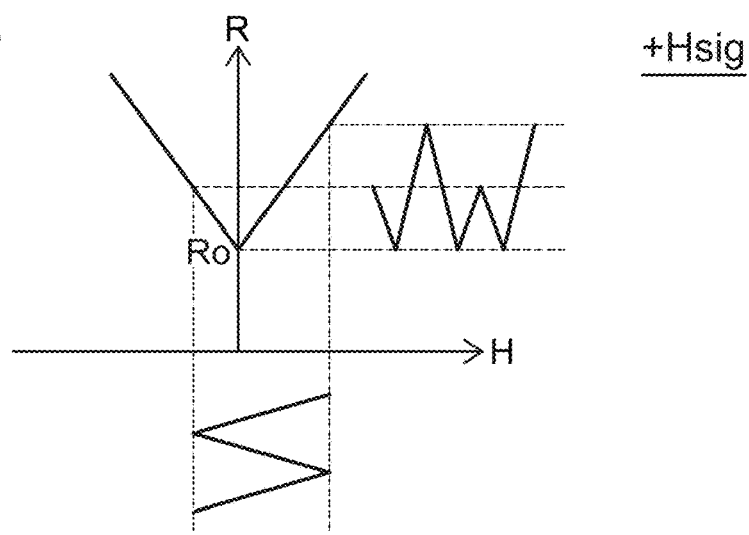
Figure 4C:
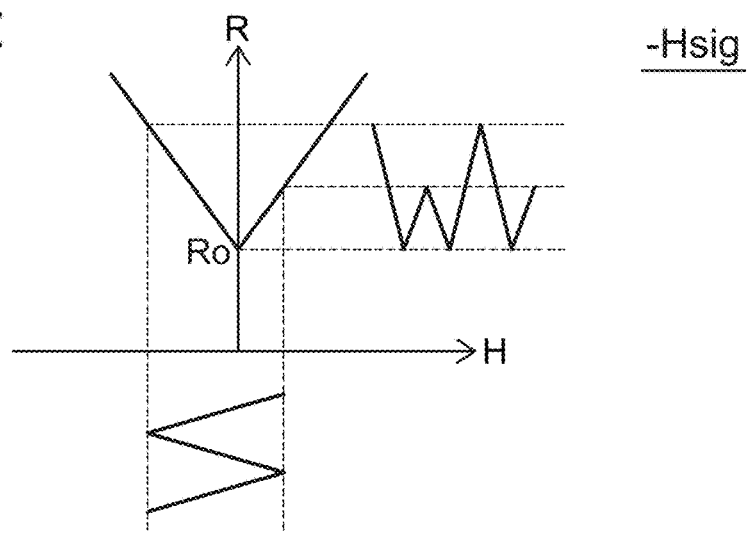

FIGS. 4A to 4C are graphs illustrating characteristics of the sensor according to the first embodiment.

FIG. 4A shows the characteristics when a signal magnetic field Hsig (external magnetic field) applied to the first magnetic element 11E is 0. FIG. 4B shows the characteristics when the signal magnetic field Hsig is positive. FIG. 4C shows the characteristics when the signal magnetic field Hsig is negative. These figures show the relationship between the magnetic field H and the resistance R (corresponding to the electrical resistance Rx).

As shown in FIG. 4A, when the signal magnetic field Hsig is 0, the resistance R exhibits a characteristic symmetric with respect to the positive and negative magnetic fields H. When the alternating magnetic field Hac is zero, the resistance R is a low resistance Ro. For example, the magnetization of the magnetic layer included in the first magnetic element 11E rotates in substantially the same manner with respect to the positive and negative magnetic fields H. Therefore, a symmetrical change in resistance can be obtained. The fluctuation of the resistance R with respect to the alternating magnetic field Hac has the same value with positive and negative polarities. The period of change of the resistance R is ½ times the period of the alternating magnetic field Hac. The frequency of change of the resistance R is twice the frequency of the alternating magnetic field Hac. The change in resistance R has substantially no frequency component of the alternating magnetic field Hac.

As shown in FIG. 4B, when a positive signal magnetic field Hsig is applied, the characteristic of the resistance R shifts to the side of the positive magnetic field H. When the alternating magnetic field Hac is in the positive side, for example, the resistance R becomes high. When the alternating magnetic field Hac is in the negative side, the resistance R becomes low.

As shown in FIG. 4C, when a negative signal magnetic field Hsig is applied, the characteristic of the resistance R shifts to the side of the negative magnetic field H. When the alternating magnetic field Hac is in the positive side, for example, the resistance R becomes low. When the alternating magnetic field Hac is in the negative side, the resistance R becomes high.

When a signal magnetic field Hsig with some amplitude is applied, the resistance R changes differently with respect to the positive and negative sides of the alternating magnetic field Hac. A component with the frequency of the alternating magnetic field Hac in the output signal corresponds to the signal magnetic field Hsig.

The above characteristics are obtained when the signal magnetic field Hsig does not change with time. When the signal magnetic field Hsig changes with time at a frequency lower than that of the alternating magnetic field Hac, it becomes as follows. The frequency of the signal magnetic field Hsig is defined as the signal frequency fsig. The frequency of the alternating magnetic field Hac is defined as the alternating frequency fac. An output signal corresponding to the signal magnetic field Hsig is located at a frequency of fac±fsig.

When the signal magnetic field Hsig changes with time, the signal frequency fsig is, for example, not more than 1 kHz. On the other hand, the alternating frequency fac is sufficiently higher than the signal frequency fsig. For example, the alternating frequency fac is not less than 10 times the signal frequency fsig.

For example, the signal magnetic field Hsig can be detected with high accuracy by extracting a component with the same frequency as the frequency of the alternating magnetic field Hac from the output signal. In the sensor 110 according to the embodiment, the external magnetic field Hex (signal magnetic field Hsig) generated from the detection object 80 can be detected with high sensitivity by utilizing such characteristics.

Such characteristics are obtained in the first element 10A and the second element 10B. A position of the first element 10A and a position of the second element 10B are different. The distance from the detection object 80 differs between the first element 10A and the second element 10B. For example, the first element 10A is far from the detection object 80, and the second element 10B is close to the detection object 80. In this case, the detection magnetic field (for example, the signal magnetic field Hsig) generated from the detection object 80 is applied to the first element 10A with a low strength. On the other hand, the detection magnetic field (for example, signal magnetic field Hsig) generated from the detection object 80 is applied to the second element 10B with a high strength.

By detecting the difference between the signals obtained from the first element 10A and the second element 10B, a magnetic field other than the detection signal generated from the detection object 80 (for example, noise) can be effectively removed. The signal magnetic field generated from the target object target 80 can be detected with higher accuracy.

As described above, in the embodiment, first, the differential signal S3 is obtained. The signal S3 corresponds to the difference between the first signal S1 corresponding to the change in the first electrical resistance of the first magnetic element 11E of the first element 10A and the second signal S2 corresponding to the change in the second electrical resistance of the first magnetic element 11E of the second element 10B. After that, the signal S3 is demodulated by the phase-detection with reference to the AC signal (Rf1 in FIG. 1). As a result, noise can be further suppressed. It is possible to provide a sensor whose characteristics can be improved.

On the other hand, as a reference example, the configuration is conceivable in which the first signal S1 and the second signal S2 is demodulated respectively by phase detection and then the difference between the two signals is obtained. In this case, it is found that the noise reduction is insufficient. A reference example will be described below.

Figure 5:
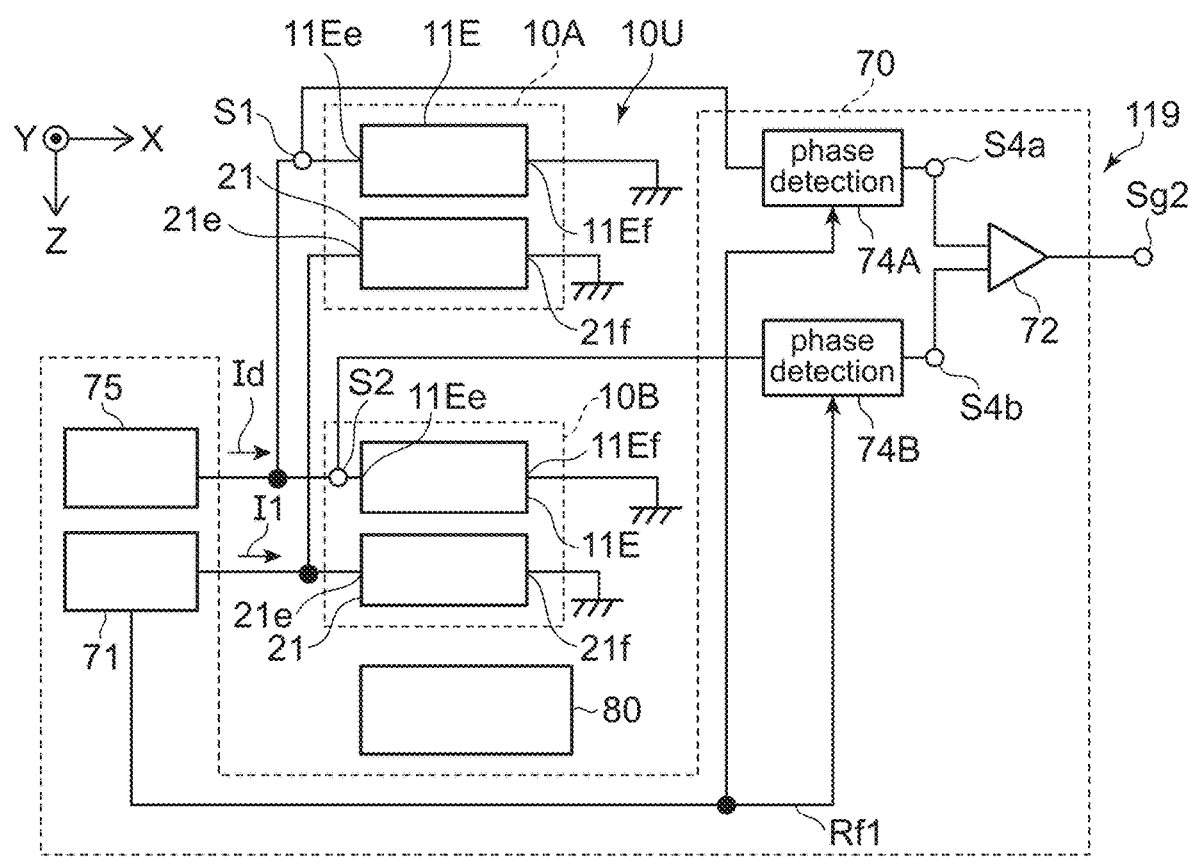
FIG. 5 is a schematic view illustrating a sensor according to a reference sample.

FIG. 5 is a schematic view illustrating a sensor according to a reference sample.

As shown in FIG. 5, a sensor 119 according to the reference example is provided with the element part 10U and the control circuit part 70. In the sensor 119, the first signal S1 corresponding to the change in the first electrical resistance of the first magnetic element 11E of the first element 10A is detected by the phase detection circuit 74A, and a phase detection signal S4a is obtained. The second signal S2 corresponding to the change in the second electrical resistance of the first magnetic element 11E of the second element 10B is detected by the phase detection circuit 74B, and a phase detection signal S4b is obtained. The differential circuit 72 derives an output signal Sg2 corresponding to the difference between the phase detection signal S4a and the phase detection signal S4b.

Hereinafter, examples of the characteristics of the sensor 110 according to the embodiment and the sensor 119 according to the reference example will be described.

Figure 6A:
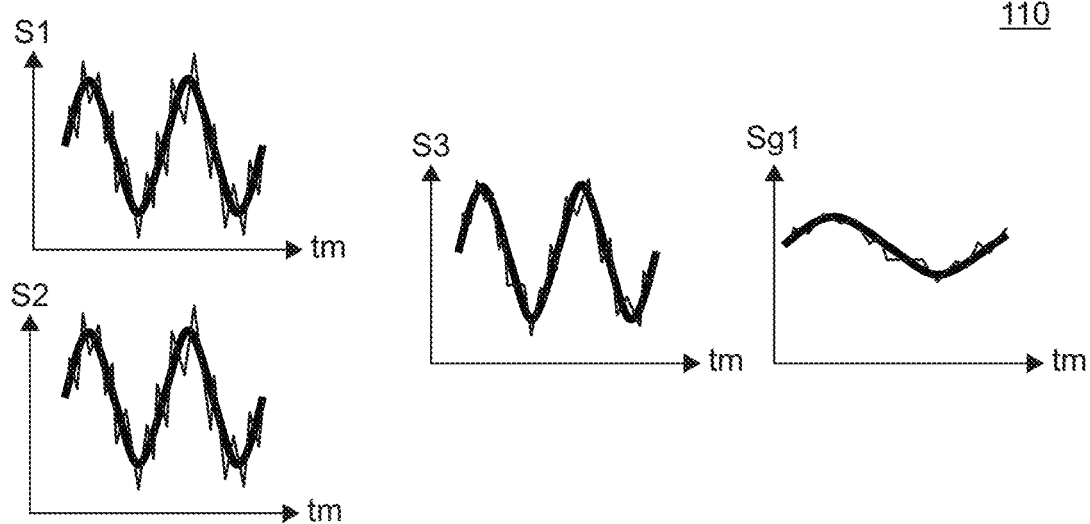
Figure 6B:
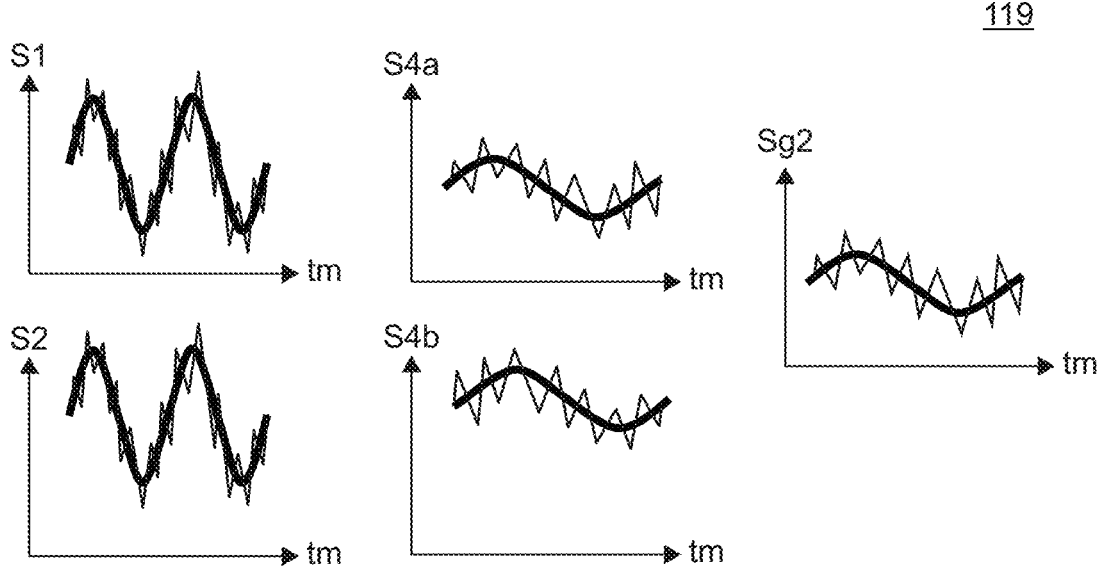

FIGS. 6A and 6B are schematic views illustrating characteristics of the sensors.

FIG. 6A corresponds to the sensor 110. FIG. 6B corresponds to the sensor 119. The horizontal axis of these figures is time tm.

As shown in FIG. 6A, in the sensor 110, each of the first signal S1 and the second signal S2 includes, for example, a component having a large amplitude and a component having a small amplitude. The component having a large amplitude is a signal in which the signal field from the detection object 80 is modulated by the alternating magnetic field Hac. The component having a small amplitude is, for example, noise (AC noise) included in the first current I1. The AC noise included in each of the first signal S1 and the second signal S2 is in phase. Therefore, in the sensor 110, the AC noise is reduced at the differential signal S3. The AC noise is small in the output signal Sg1 obtained by phase-detecting the differential signal S3 with the reference signal of the alternating magnetic field Hac. The AC noise can be reduced in the output signal Sg1 obtained by demodulation.

As shown in FIG. 6B, also in the sensor 119, each of the first signal S1 and the second signal S2 includes, for example, a component having a large amplitude (a signal field from the detection object 80 modulated by an alternating magnetic field Hac), and a small amplitude component (AC noise). In the sensor 119, the first signal S1 and the second signal S2 are demodulated by the phase-detection with the reference signal of the alternating magnetic field Hac, respectively, and the phase detection signal S4a and the phase detection signal S4b are derived. Each of the S4a and the S4b is demodulated including the AC noise. The components corresponding to the AC noise are not in phase in the signal S4a and the signal S4b since each signal has already been demodulated. Therefore, in the output signal Sg2 corresponding to the difference between the phase detection signal S4a and the phase detection signal S4b, the component corresponding to the AC noise remains. In the sensor 119, it is difficult to reduce the AC noise in the output signal Sg2.

In this way, noise can be further reduced by performing phase detection of the signal S3, which corresponds to the difference between the first signal S1 and the second signal S2. The AC noise included in the first current I1 can be effectively reduced. On the other hand. The AC noise included in the first current I1 is difficult to be reduced in the reference example in which the order of the phase detection and the differentiation is reversed. In the embodiment, under the configuration in which the first current I1 is supplied to the first conductive member 21, a special effect can be obtained, that is the AC noise generated in the configuration can be reduced. It is possible to provide a sensor whose characteristics can be improved.

FIGS. 7A to 7H are schematic views illustrating characteristics of the sensors.

FIGS. 7A to 7D correspond to the sensor 110. FIGS. 7E to 7H correspond to the sensor 119. These figures correspond to FFT (Fast Fourier Transform) processed signals. The horizontal axis of these figures is frequency fr. The vertical axis of these figures corresponds to the signal strength SS.

Figure 7A:
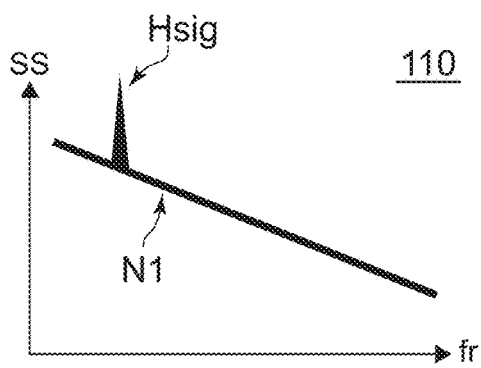
FIGS. 7A to 7H are schematic views illustrating characteristics of the sensors.

As shown in FIG. 7A, in the sensor 110, noise N1 is present in addition to the signal magnetic field Hsig of the detection object 80. The noise N1 is, for example, noise from the environment.

Figure 7E:
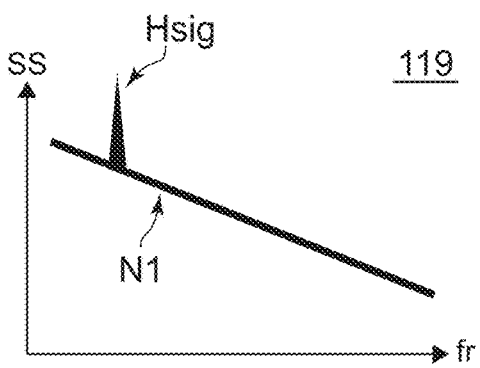
Figure 7B:
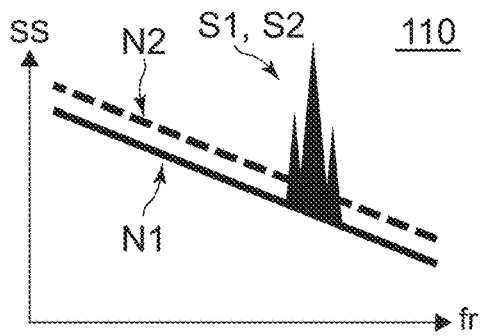

As shown in FIG. 7B, the signal magnetic field Hsig is converted by the first current I1 including the AC component, and the first signal S1 and the second signal S2 are obtained. These signals include AC noise N2 included in the first current I1.

Figure 7F:
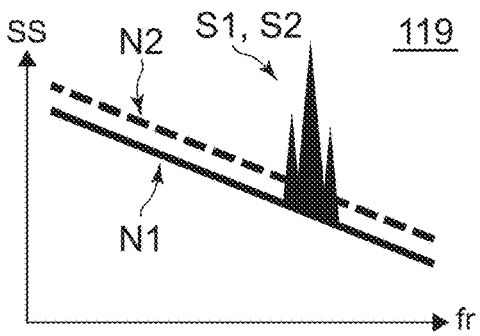
Figure 7C:
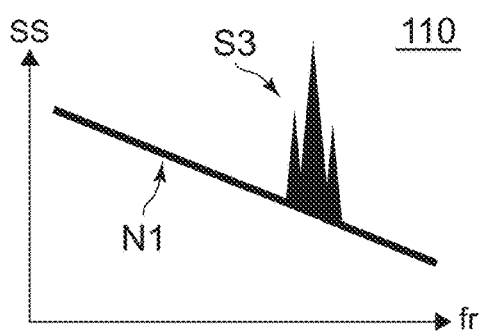

As shown in FIG. 7C, the AC noise N2 is reduced in the differential signal S3 corresponding to the difference between the first signal S1 and the second signal S2.

Figure 7G:
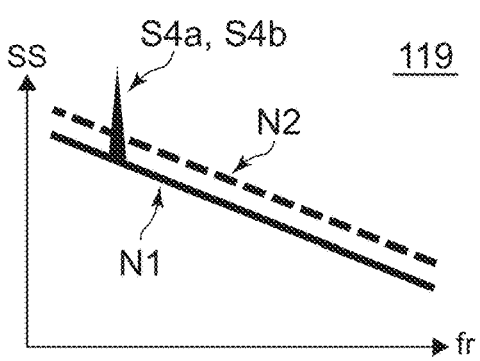
Figure 7D:
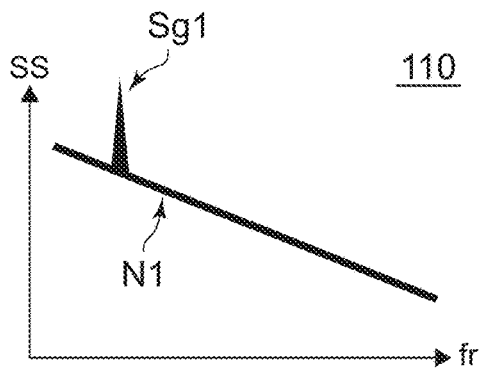

As shown in FIG. 7D, the AC noise N2 is suppressed in the output signal Sg1 obtained by phase-detecting the differential signal S3.

As shown in FIG. 7E, the sensor 119 also has the noise N1 in addition to the signal magnetic field Hsig of the detection object 80.

As shown in FIG. 7F, the signal magnetic field Hsig is converted by the first current I1 including the AC component, and the first signal S1 and the second signal S2 are obtained. These signals include the AC noise N2 included in the first current I1.

As shown in FIG. 7G, the phase detection signal S4a and the phase detection signal S4b obtained by the phase-detection of each of the first signal S1 and the second signal S2 include the noise N2.

Figure 7H:
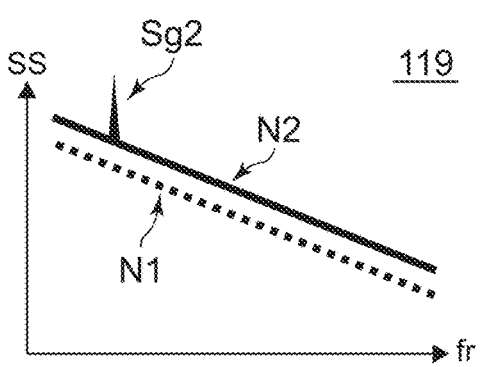

As shown in FIG. 7H, the AC noise N2 remains in the output signal Sg2 corresponding to the difference between the phase detection signal S4a and the phase detection signal S4b. In the sensor 119, it is difficult to reduce the AC noise N2.

In this way, for example, the alternating magnetic field based on the first current is applied to the magnetic element. As a result, the detection magnetic field is modulated to the high frequency region. Noise (for example, AC noise N2) may be included in the first current I1. In this case, the AC noise N2 is also modulated in the high frequency region together with the detection magnetic field.

In the reference example, the modulated signal including the AC noise N2 is detected (demodulated), The AC noise N2 remains in the demodulated signal. The phases of the demodulated AC noise N2 are different between the first element 10A and the second element 10B. Therefore, the AC noise N2 cannot be removed in the subsequent differential processing. Therefore, in the reference example, the AC noise N2 remains in the detection signal. Noise is large.

On the other hand, in the embodiment, the phase of the AC noise N2 is the same in the first element 10A and the second element 10B. The modulated signals including the AC noise N2 are then differentiated. As a result, the AC noise N2 is removed. After that, the differential signal S3 in which the AC noise N2 is reduced is detected (demodulated). Therefore, in the embodiment, the AC noise N2 is reduced in the output signal Sg1.

According to the embodiment, for example, noise-suppressed detection becomes possible. According to the embodiment, it is possible to provide a sensor whose characteristics can be improved.

Hereinafter, some examples of the element part 10U according to the embodiment will be described.

Figure 8:
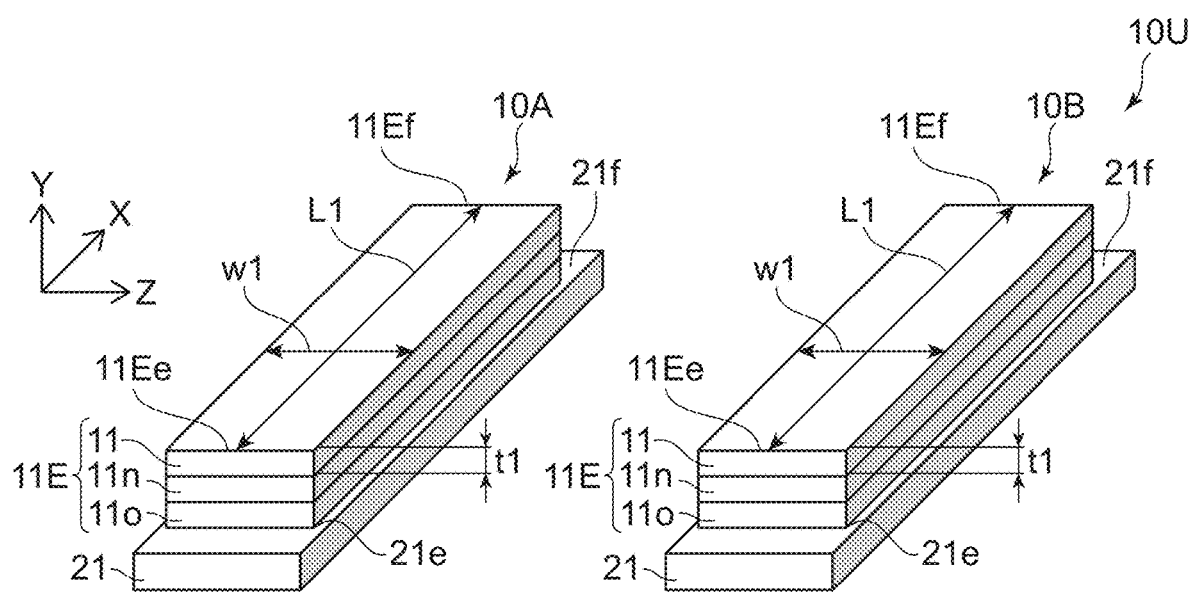
FIG. 8 is a schematic perspective view illustrating the sensor according to the first embodiment.

FIG. 8 is a schematic perspective view illustrating the sensor according to the first embodiment.

As shown in FIG. 8, in the first element 10A, the first magnetic element 11E includes a first magnetic layer 11, a first opposed magnetic layer 11o, and a first non-magnetic layer 11n. The first non-magnetic layer 11n is provided between the first magnetic layer 11 and the first opposed magnetic layer 11o.

The second direction from the first opposed magnetic layer 11o to the first magnetic layer 11 crosses the first direction from the one end part 11Ee of the first magnetic element 11E to the other end part 11Ef of the first magnetic element 11E. The first direction is, for example, the X-axis direction. The second direction is, for example, the Y-axis direction.

A length of the first magnetic layer 11 along the first direction (X-axis direction) is defined as a length L1. A length of the first magnetic layer 11 along the third direction is defined as a length w1. The third direction crosses the plane including the first and second directions. The third direction is, for example, the Z-axis direction.

A length of the first magnetic layer 11 along the second direction (Y-axis direction) is defined as a length t1. The length L1 is longer than the length t1. The length w1 is, for example, longer than the length t1. In the embodiment, the length L1 is, for example, not less than 0.1 μm and not more than 10 mm. The length w1 is, for example, not less than 0.01 μm and not more than 1 mm. The length t1 is, for example, not less than 1 nm and not more than 100 nm. It is easy to obtain good even function characteristics.

For example, the first magnetic layer 11 and the first opposed magnetic layer 11o include at least one selected from the group consisting of Fe, Co and Ni. For example, the first non-magnetic layer 11n includes at least one selected from the group consisting of Cu, Au and Ag. The first magnetic element 11E is, for example, a GMR (Giant Magneto Resistance) element. The first magnetic element 11E may be, for example, a TMR (Tunnel Magneto Resistance) element.

As shown in FIG. 8, in the second element 10B, the same configuration as that of the first element 10A may be applied.

As shown in FIG. 8, the second element 10B is separated from the first element 10A in the third direction (for example, the Z-axis direction). For example, the position of the first element 10A in the third direction (Z-axis direction) is different from the position of the second element 10B in the third direction. For example, the distance along the third direction between the detection object 80 and the first element 10A is different from the distance along the third direction between the detection object 80 and the second element 10B. For example, the strength of the magnetic field from the detection object 80 differs between the first element 10A and the second element 10B. The noise N1 is substantially the same between the first element 10A and the second element 10B.

In embodiments, each of the first element 10A and the second element 10B may include a half bridge or a full bridge.

Figures 9A, 9B:
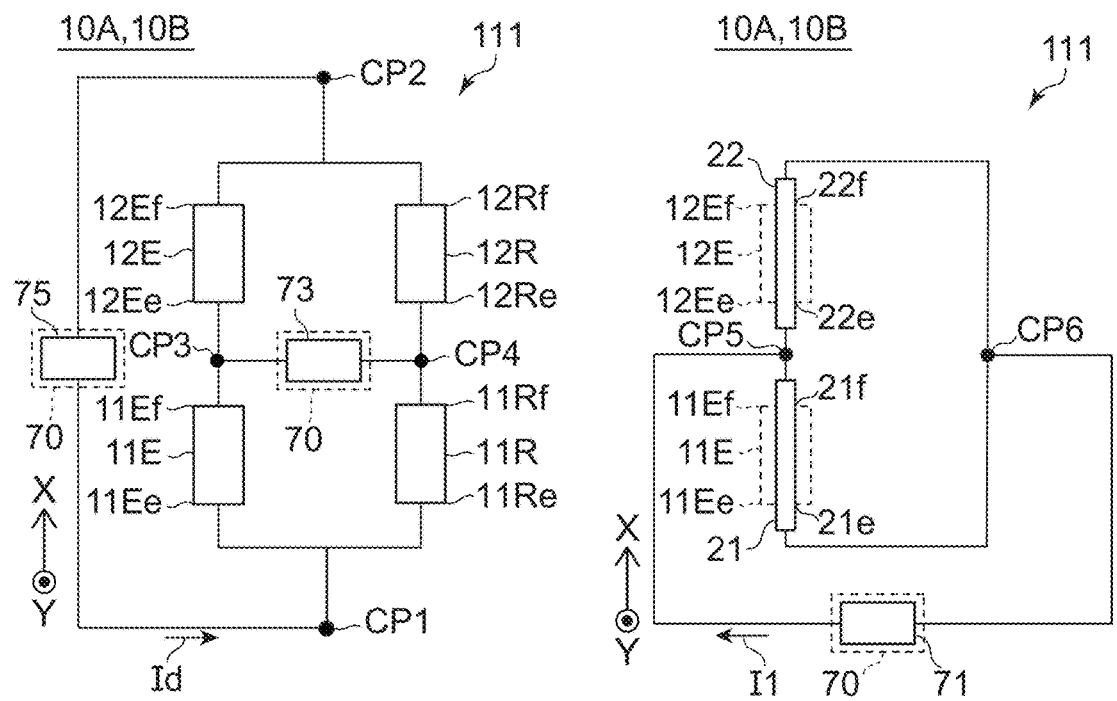
FIGS. 9A and 9B are schematic plan views illustrating a sensor according to the first embodiment.

FIGS. 9A and 9B are schematic plan views illustrating a sensor according to the first embodiment.

These figures show an example of each configuration of the first element 10A and the second element 10B. The configuration of the second element 10B is the same as the configuration of the first element 10A. As described above, each of the first element 10A and the second element 10B includes the first magnetic element 11E and the first conductive member 21.

As shown in FIGS. 9A and 9B, in a sensor 111, each of the first element 10A and the second element 10B further includes a second magnetic element 12E, a second conductive member 22, a first resistance element 11R, and a second resistance element 12R. In FIGS. 9A and 9B, these elements are drawn as separate figures for the sake of clarity.

As shown in FIG. 9A, the one end part 11Ee of the first magnetic element 11E is electrically connected to one end part 11Re of the first resistance element 11R. One end part 12Ee of the second magnetic element 12E is electrically connected to the other end part 11Ef of the first magnetic element 11E. One end part 12Re of the second resistance element 12R is electrically connected to other end part 11Rf of the first resistance element 11R, Other end part 12Ef of the second magnetic element 12E is electrically connected to other end part 12Rf of the second resistance element 12R.

The first magnetic element 11E, the second magnetic element 12E, the first resistance element 11R, and the second resistance element 12R are connected as a bridge circuit.

As shown in FIG. 9A, the control circuit part 70 may further include a detection circuit 73. The detection circuit 73 is configured to detect a change in the first potential between the other end 11Ef (for example, connection point CP3) of the first magnetic element 11E of the first element 10A and the other end 11Rf (for example, connection point CP4) of the first resistance element 11R of the first element 10A as the first signal S1. The detection circuit 73 is configured to detect a change in the second potential between the other end 11Ef (for example, connection point CP3) of the first magnetic element 11E of the second element 10B and the other end 11Rf (for example, connection point CP4) of the first resistance element 11R of the second element 10B as the second signal S2.

As shown in FIG. 9A, for example, the control circuit part 70 may further include an element current circuit 75. The element current circuit 75 is configured to supply the element current Id between the connection point CP1 between the one end part 11Ee of the first magnetic element 11E of the first element 10A and the one end part 11Re of the first resistance element 11R of the first element 10A, and the connection point CP2 between the other end part 12Ef of the magnetic element 12E of the first element 10A and the other end part 12Rf of the second resistance element 12R of the first element 10A.

As shown in FIG. 9B, the element current circuit 75 is configured to supply the element current Id between the connection point CP1 between the one end part 11Ee of the first magnetic element 11E of the second element 10B and the one end part 11Re of the first resistance element 11R of the second element 10B, and the connection point CP2 between the other end part 12Ef of the second magnetic element 12E of the second element 10B and the other end part 12Rf of the second resistance element 12R of the second element 10B.

As shown in FIG. 9B, at least a part of the first conductive member 21 may overlap the first magnetic element 11E. At least a part of the second conductive member 22 may overlap the first magnetic element 11E. The second conductive member 22 may be a part of the first conductive member 21, In this case, the second conductive member 22 is not provided. The boundary between the second conductive member 22 and the first conductive member 21 may be clear or unclear. The first current circuit 71 is configured to supply the first current I1 to the first conductive member 21 and the second conductive member 22.

As shown in FIG. 9B, in each of the first element 10A and the second element 10B, the first conductive member 21 includes the first conductive member one part 21e corresponding to the one end part 11Ee of the first magnetic element 11E, and the first conductive member other part 21f corresponding to the other end part 11Ef of the first magnetic element 11E.

In each of the first element 10A and the second element 10B, the second conductive member 22 includes a second conductive member one part 22e corresponding to the one end part 12Ee of the second magnetic element 12E and a second conductive member other part 22f corresponding to other end part 12Ef of the second magnetic element 12E.

In each of the first element 10A and the second element 10B, when the first current I1 flows in the orientation from the first conductive member other part 21f to the first conductive member one part 21e, the first current I1 flows in the orientation from the second conductive member one part 22e to the second conductive member other part 22f, In the first conductive member 21 and the second conductive member 22, the orientations of the first current I1, are opposite. In the first conductive member 21 and the second conductive member 22, the phases of the first current I1 are opposite.

As shown in FIG. 9B, for example, the first current circuit 71 supplies the first current I1 between the connection point CP5 between the other end part 11Ef of the first magnetic element 11E and the one end part 12Ee of the second magnetic element 12E, and the connection point CP6 between the one end part 11Ee of the first magnetic element 11E and the other end part 12Ef of the second magnetic element 12E.

FIG. 10, and FIGS. 11A to 11D are schematic plan views illustrating a sensor according to the first embodiment.

These figures show an example of each configuration of the first element 10A and the second element 10B. The configuration of the second element 10B is the same as the configuration of the first element 10A. As described above, each of the first element 10A and the second element 10B includes the first magnetic element 11E and the first conductive member 21.

Figure 10:
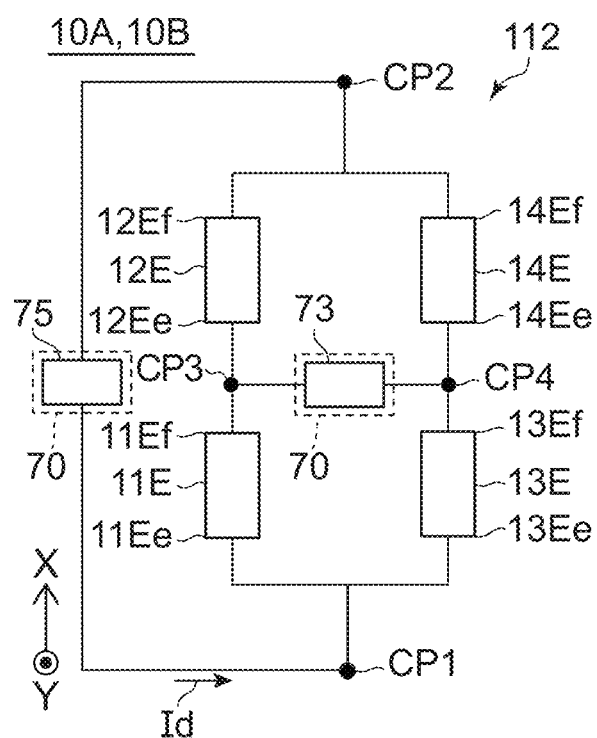
FIG. 10 is a schematic plan view illustrating a sensor according to the first embodiment.
Figure 11A:
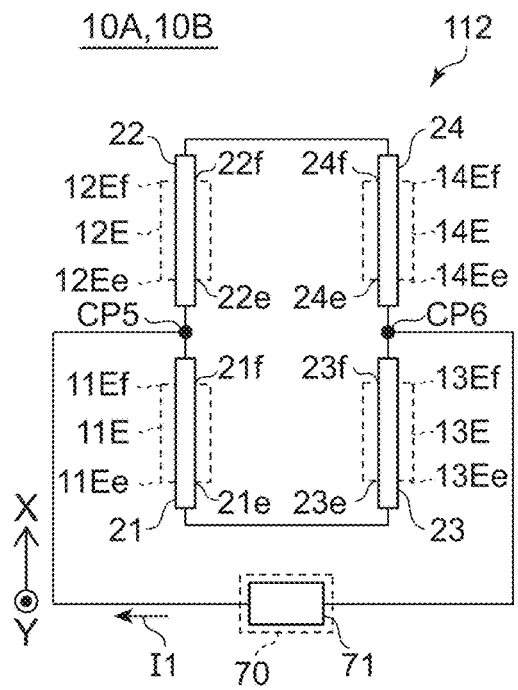
FIGS. 11A to 11D are schematic plan views illustrating sensors according to the first embodiment.

As shown in FIGS. 10 and 11A, in a sensor 112, the first dement 10A and the second dement 10B further includes second to fourth magnetic dements 12E to 14E and second to fourth conductive members 22 to 24. In these figures, these elements are drawn as separate figures for the sake of clarity.

As shown in FIG. 10, the one end part 11Ee of the first magnetic dement 11E is electrically connected to one end part 13Ee of the third magnetic dement 13E. The one end part 12Ee of the second magnetic element 12E is electrically connected to the other end part 11Ef of the first magnetic element 11E. One end part 14Ee of the fourth magnetic element 14E is electrically connected to the other end part 13Ef of the third magnetic element 13E. The other end part 12Ef of the second magnetic element 12E is electrically connected to the other end part 14Ef of the fourth magnetic element 14E.

As shown in FIG. 11A, the first current circuit 71 is configured to supply the first current I1 to the first conductive member 21, the second conductive member 22, the third conductive member 23, and the fourth conductive member 24.

As shown in FIG. 10, the control circuit part 70 may further include the detection circuit 73. The detection circuit 73 is configured to detect a change in the first potential between the other end part 11Ef (for example, connection point CP3) of the first magnetic element 11E of the first element 10A and the other end part 13Ef (for example, connection point CP4) of the third magnetic element 13E of the first element 10A as the first signal S1.

The detection circuit 73 is configured to detect a change in the second potential between the other end part 11Ef (connection point CP3) of the first magnetic element 11E of the second element 10B and the other end part 13Ef (for example, connection point CP4) of the third magnetic element 13E of the second element 10B as the second signal S2.

As shown in FIG. 10, for example, the control circuit part 70 may further include the element current circuit 75. The element current circuit 75 is configured to supply the element current Id between the connection point CP1 between the one end part 11Ee of the first magnetic element 11E of the first element 10A and the one end part 13Ee of the third magnetic element 13E of the first element 10A, and the connection point CP2 between the other end part 12Ef of the second magnetic element 12E of the first element 10A and the other end part 14Ef of the fourth magnetic element 14E of the first element 10A.

The element current circuit 75 is configured to supply the element current Id between the connection point CP1 between the one end part 11Ee of the first magnetic element 11E of the second element 10B and the one end part 13Ee of the third magnetic element 13E of the second element 10B, and the connection point CP2 between the other end part 12Ef of the second magnetic element 12E of the second element 10B and the other end part 14Ef of the fourth magnetic element 14E of the second element 10B.

As shown in FIG. 11A, in each of the first element 10A and the second element 10B, the first conductive member 21 includes the first conductive member one part 21e corresponding to the one end part 11Ee of the first magnetic element 11E and the first conductive member other part 21f corresponding to the other end part 11Ef of the first magnetic element 11E. In each of the first element 10A and the second element 10B, the second conductive member 22 includes the second conductive member one part 22e corresponding to the one end part 12Ee of the second magnetic element 12E and the second conductive member other part 22f corresponding to the other end part 12Ef of the second magnetic element 12E. In each of the first element 10A and the second element 10B, the third conductive member 23 includes a third conductive member one part 23e corresponding to the one end part 13Ee of the third magnetic element 13E and a third conductive member other part 23f corresponding to the other end part 13Ef of the third magnetic element 13E. In each of the first element 10A and the second element 10B, the fourth conductive member 24 includes a fourth conductive member one part 24e corresponding to the one end part 14Ee of the fourth magnetic element 14E and a fourth conductive member other part 24f corresponding to the other end part 14Ef of the fourth magnetic element 14E.

When the first current I1 is flowing in the orientation from the first conductive member other part 21f to the first conductive member one part 21e, the first current I1 flows in the orientation from the second conductive member one part 22e to the second conductive member other part 22f, the first current I1 flows in the orientation from the third conductive member one part 23e to the third conductive member other part 23f, and the first current I1 flows in the orientation from the fourth conductive member other part 24f to the fourth conductive member one part 24e.

As shown in FIG. 11A, in the sensor 112, the first current circuit 71 supplies the first current I1 between the connection point CP5 of the first conductive member other part 21f and the second conductive member one part 22e, and the connection point CP6 of the third conductive member other part 23f and the fourth conductive member one part 24e.

Figure 11B:
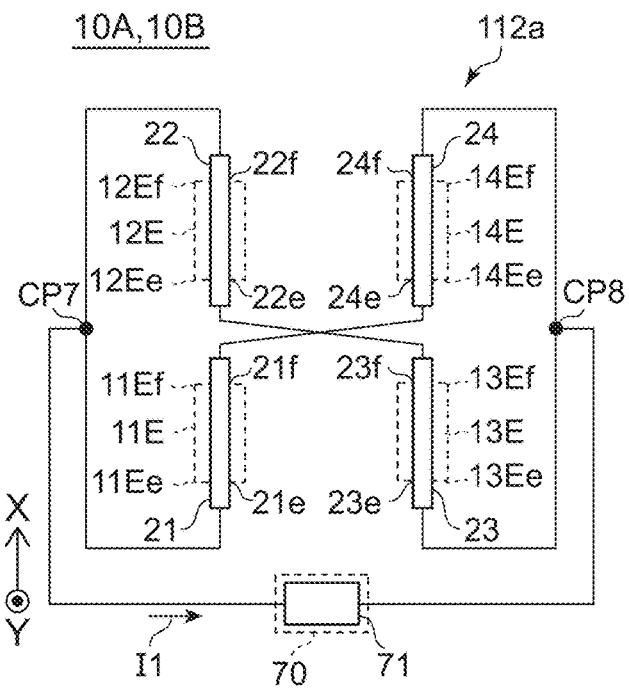
Figure 11C:
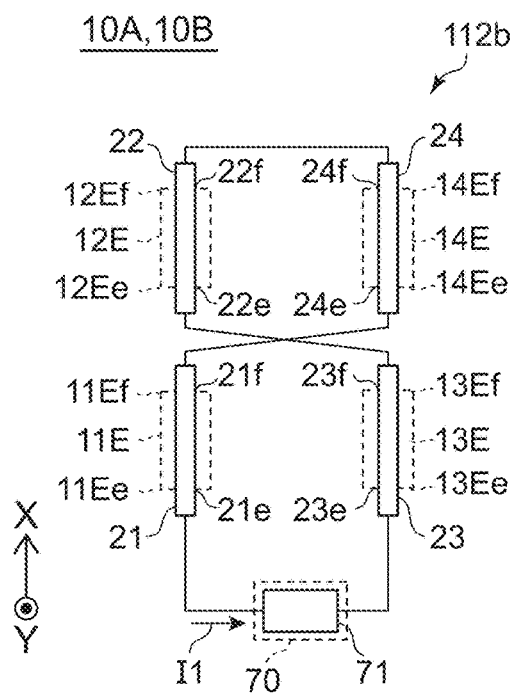
Figure 11D:
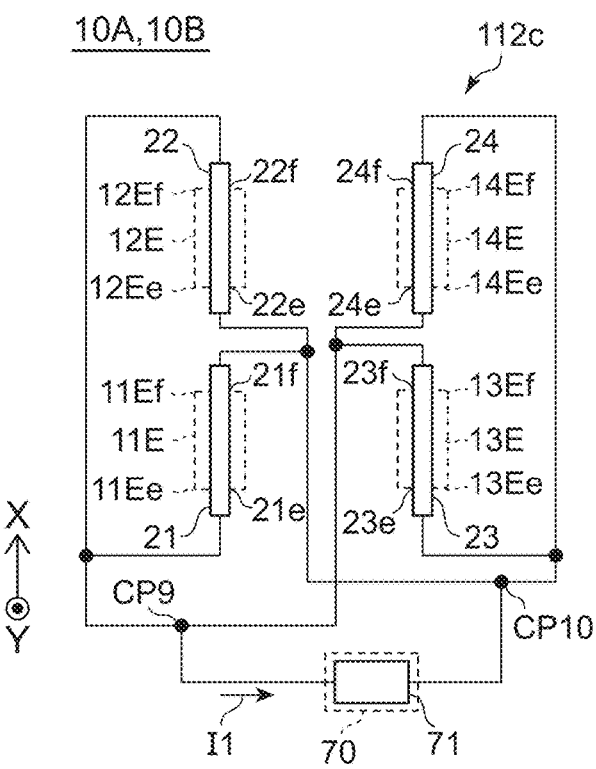

As shown in FIGS. 11B to 11D, in sensors 112a to 112c, the configurations of the first to fourth magnetic elements 11E to 14E are the same as those in the sensor 112.

As shown in FIG. 11B, in the sensor 112a, the first current circuit 71 supplies the first current I1 between the connection point CP7 of the first conductive member one part 21e and the second conductive member other part 22f, and the connection point CP8 of the third conductive member one part 23e and the fourth conductive member other part 24f. In the sensor 112a, the first conductive member other part 21f is electrically connected to the fourth conductive member one part 24e. The second conductive member one part 22e is electrically connected to the third conductive member other part 23f.

As shown in FIG. 11C, in the sensor 112b, the first current circuit 71 supplies the first current I1 between the first conductive member one part 21e and the third conductive member one part 23e. In the sensor 112b, the first conductive member other part 21f is electrically connected to the fourth conductive member one part 24e. The second conductive member part 22e is electrically connected to the third conductive member other part 23f. The second conductive member other part 22f is electrically connected to the fourth conductive member other part 24f.

As shown in FIG. 11D, in the sensor 112c, the first current circuit 71 supplies the first current I1 between a connection point CP9 of the first conductive member one part 21e, the second conductive member other part 22f, the third conductive member other part 23f, and the fourth conductive member one part 24e, and a connection point CP10 of the first conductive member other part 21f, the second conductive member other part 22e, the third conductive member one part 23e, and the fourth conductive member other part 24f.

Figure 12A:
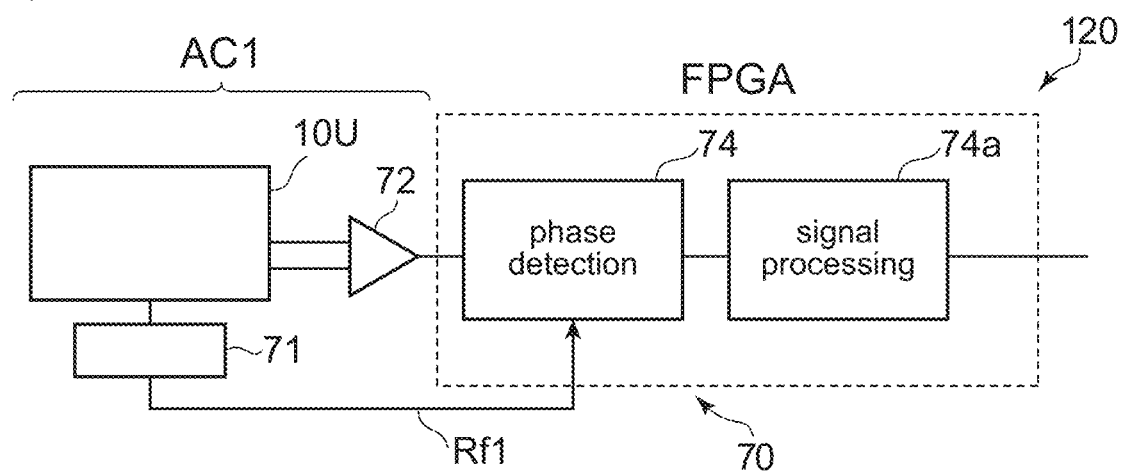
FIGS. 12A and 12B are schematic views illustrating sensors according to the first embodiment.
Figure 12B:
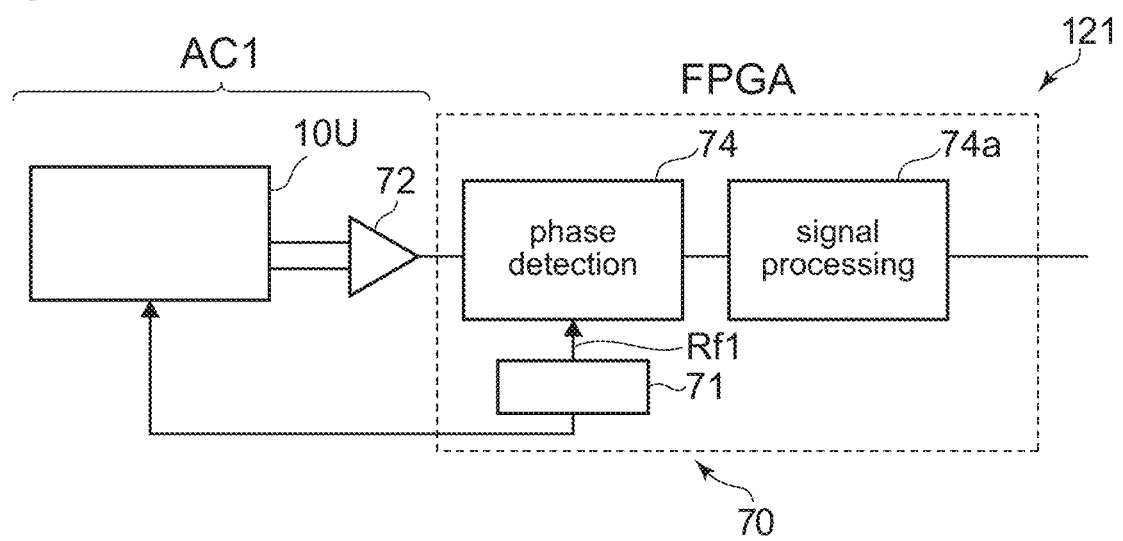

FIGS. 12A and 12B are schematic views illustrating sensors according to the first embodiment.

As shown in FIG. 12A, in a sensor 120 according to the embodiment, at least a part of the differential circuit 72 is included in an analog circuit AC1. At least a part of the phase detection circuit 74 is included in FPGA (Field Programmable Gate Array). As shown in FIG. 12A, in this example, the first current circuit 71 is included in the analog circuit AC1. As shown in sensor 120, the FPGA may include a processing circuit 74a. The processing circuit 74a processes the output signal of the phase detection circuit 74. The FPGA may be capable of processing the output signal of the phase detection circuit 74.

As shown in FIG. 12B, in a sensor 121, at least a part of the differential circuit 72 is included in the analog circuit AC1. At least a part of the phase detection circuit 74 and at least a part of the first current circuit 71 (for example, an oscillation circuit part) are included in the FPGA.

Figure 13:
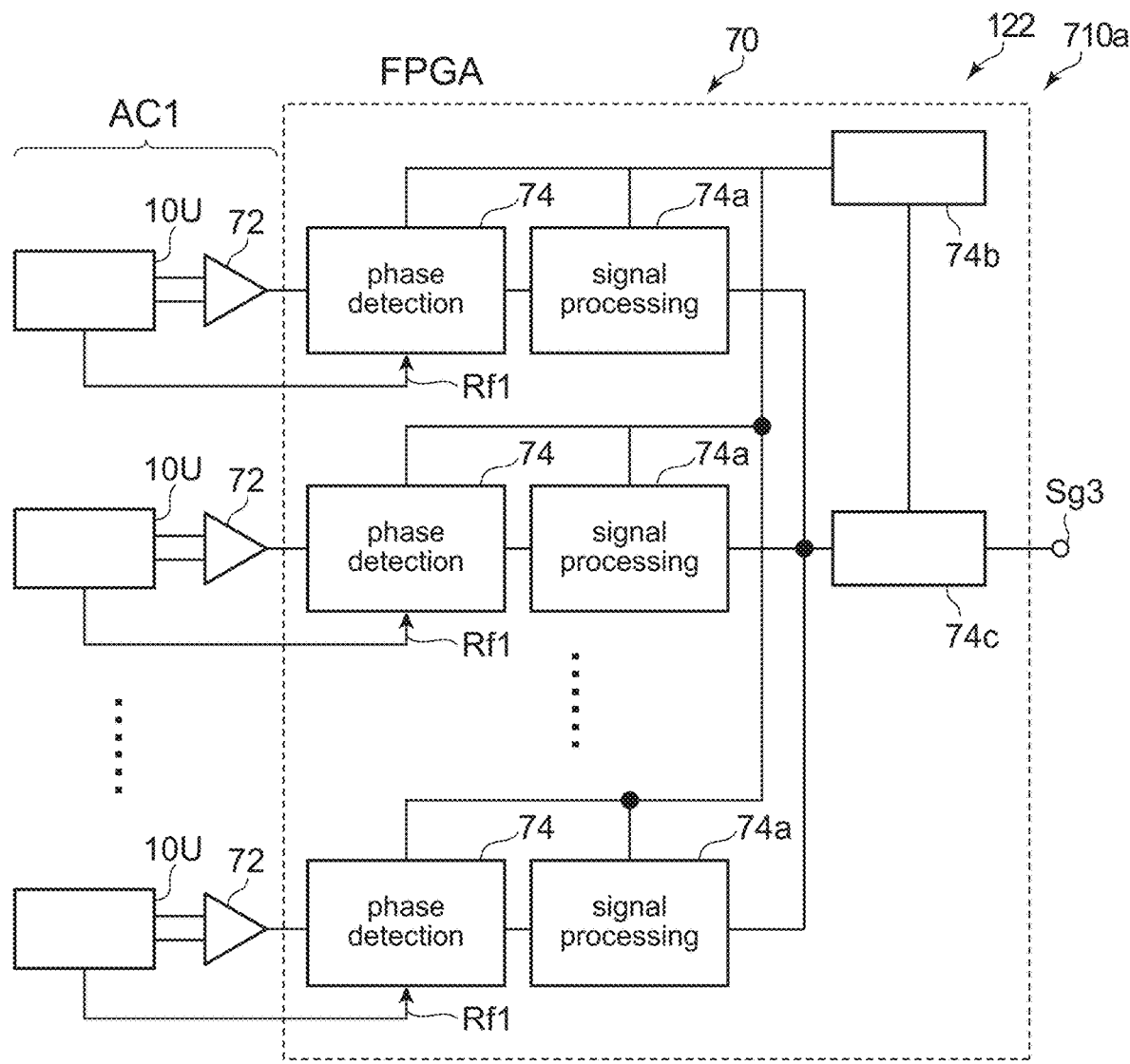
FIG. 13 is a schematic view illustrating a sensor according to the first embodiment.

FIG. 13 is a schematic view illustrating a sensor according to the first embodiment.

As shown in FIG. 13, a sensor 122 according to the embodiment includes multiple element parts 10U. The control circuit part 70 includes multiple differential circuits 72 corresponding to the multiple element parts 10U. At least a part of each of the multiple differential circuits 72 is included in the analog circuit AC1.

In this example, the control circuit part 70 includes multiple phase detection circuits 74 corresponding to each of the multiple differential circuits 72. The multiple phase detection signals 74 are included in the FPGA.

Further, in this example, multiple processing circuits 74a are provided corresponding to the multiple phase detection circuits 74. The multiple processing circuits 74a are included in the FPGA, for example. The multiple processing circuits 74a are configured to process the outputs of the multiple phase detection circuits 74, respectively. In this way, for example, the FPGA may be capable of processing each output signal of the multiple phase detection circuits 74.

In this example, the FPGA includes a control signal part 74b. The control signal part 74b is configured to control multiple phase detection circuits 74. The control signal part 74b may be able to control multiple processing circuits 74a, In this way, the FPGA may be able to control multiple phase detection circuits 74.

The FPGA may further include, for example, a signal processor 74c. The signal processor 74c is configured to perform integrated signal processing on signals (data) obtained from each of the multiple processing circuits 74a, for example. The signal processor 74c may further perform array signal processing on the signal (data) for which the integrated signal processing has been performed. The signal processor 74c may perform imaging processing of the array-processed signal (data). The signal processor 74c may analyze the imaged signal (data). The signal processor 74c is configured to output the result of performing these processes as an output signal Sg3.

An inspection device 710a according to the embodiment may include at least a part of the control circuit part 70. The inspection device 710a may include multiple element parts 10U, a part of the control circuit part 70, and a signal processor 74c.

Second Embodiment

The second embodiment relates to an inspection device. As will be described later, the inspection device may include a diagnostic device.

Figure 14:
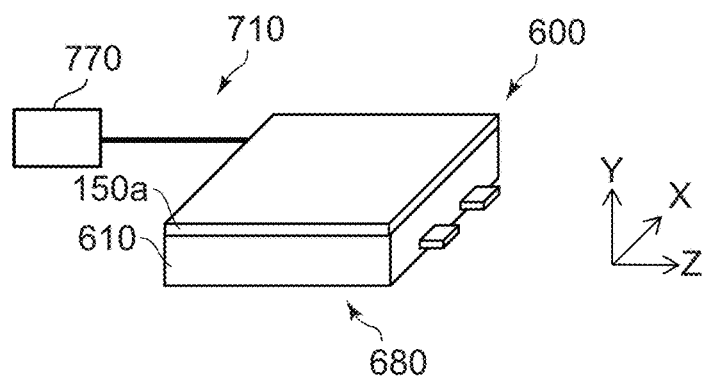
FIG. 14 is a schematic perspective view showing an inspection device according to a second embodiment.

FIG. 14 is a schematic perspective view illustrating an inspection device according to a second embodiment.

As shown in FIG. 14, an inspection device 710 according to the embodiment includes a sensor 150a and a processor 770. The sensor 150a may be the sensor according to any one of the first embodiments and a modification thereof. The processor 770 processes an output signal obtained from the sensor 150a. The processor 770 may compare the signal obtained from the sensor 150a with the reference value. The processor 770 can output the inspection result based on the processing result.

For example, the inspection device 710 inspects an inspection object 680, The inspection object 680 is, for example, an electronic device (including a semiconductor circuit or the like). The inspection object 680 may be, for example, a battery 610 or the like.

For example, the sensor 150a according to the embodiment may be used together with the battery 610. For example, a battery system 600 includes the battery 610 and the sensor 150a. The sensor 150a can detect the magnetic field generated by the current flowing through the battery 610.

Figure 15:
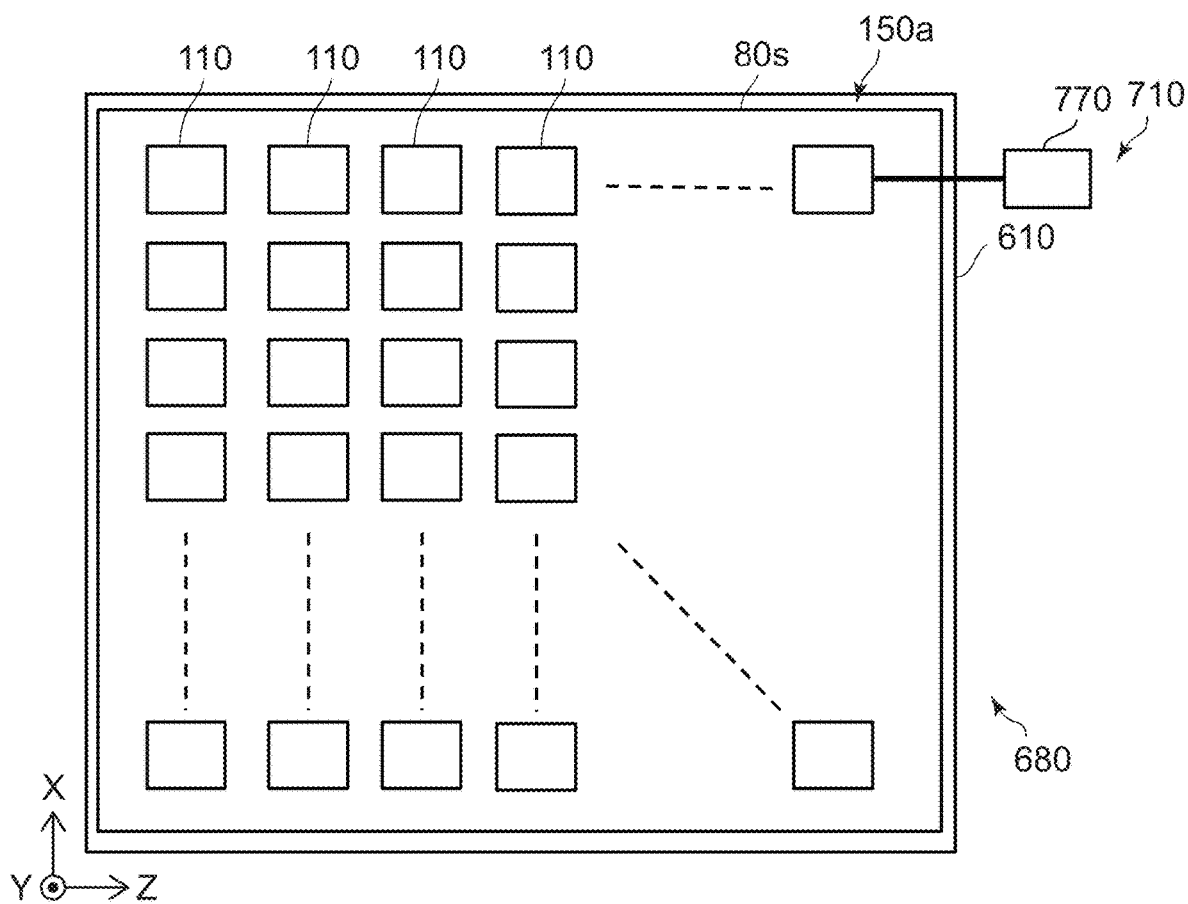
FIG. 15 is a schematic plan view showing an inspection device according to a second embodiment.

FIG. 15 is a schematic plan view illustrating the inspection device according to the second embodiment.

As shown in FIG. 15, the sensor 150a includes, for example, multiple sensors according to the embodiment. In this example, the sensor 150a includes multiple sensors (eg, sensor 110, etc.).

The multiple sensors are arranged along, for example, two directions (for example, the X-axis direction and the Y-axis direction). The multiple sensors 110 are provided, for example, on a base body.

The sensor 150a can detect the magnetic field generated by the current flowing through the inspection object 680 (for example, the battery 610 may be used), For example, when the battery 610 approaches an abnormal state, an abnormal current may start to flow through the battery 610. By detecting the abnormal current with the sensor 150a, it is possible to know the change in the state of the battery 610. For example, in a state where the sensor 150a is placed close to the battery 610, the entire battery 610 can be inspected in a short time by moving the sensor array in two directions. The sensor 150a may be used for inspection of the battery 610 in manufacturing process of the battery 610.

The sensor according to the embodiment can be applied to, for example, the inspection device 710 such as a diagnostic device.

Figure 16:
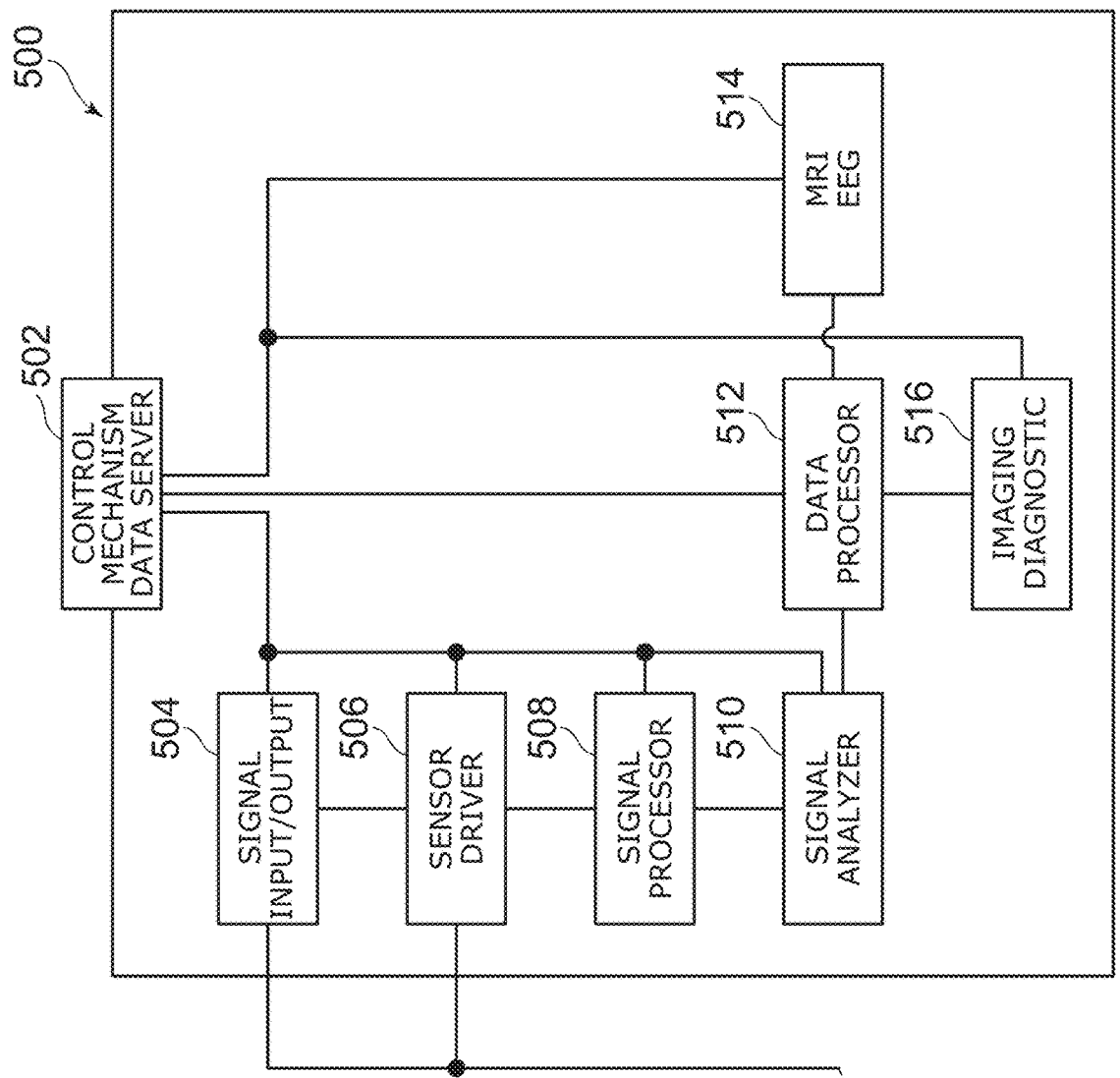
FIG. 16 is a schematic view showing a sensor and the inspection device according to the second embodiment.

FIG. 16 is a schematic view illustrating the sensor and the inspection device according to the second embodiment.

As shown in FIG. 16, a diagnostic device 500, which is an example of the inspection device 710, includes a sensor 150. The sensor 150 includes the sensors described with respect to the first embodiment and modifications thereof.

In the diagnostic apparatus 500, the sensor 150 is, for example, a magnetoencephalograph. The magnetoencephalograph detects the magnetic field generated by the cranial nerves. When the sensor 150 is used in a magnetoencephalograph, the size of the magnetic element included in the sensor 150 is, for example, not less than 1 mm and less than 10 mm.

As shown in FIG. 16, the sensor 150 (magnetoencephalogram) is attached to, for example, the head of a human body. The sensor 150 (magnetoencephalogram) includes a sensor part 301. The sensor 150 (magnetoencephalogram) may include multiple sensor parts 301. The number of the multiple sensor parts 301 is, for example, about 100 (for example, not less than 50 and not more than 150). The multiple sensor parts 301 are provided on a flexible base body 302.

The sensor 150 may include, for example, a circuit such as differential detection. The sensor 150 may include a sensor other than the sensor (for example, a potential terminal or an acceleration sensor).

A size of the sensor 150 is smaller than a size of a conventional SQUID (Superconducting Quantum Interference Device) sensor. Therefore, it is easy to install the multiple sensor parts 301. Installation of the multiple sensor parts 301 and other circuits is easy. The coexistence of the multiple sensor parts 301 and other sensors is easy.

The base body 302 may include an elastic body such as a silicone resin. For example, the multiple sensor parts 301 are provided to be connected to the base body 302. The base body 302 can be in close contact with the head, for example.

The input/output code 303 of the sensor part 301 is connected to a sensor driver 506 and a signal input/output 504 of the diagnostic device 500. The magnetic field measurement is performed in the sensor part 301 based on the electric power from the sensor driver 506 and the control signal from the signal input/output 504. The result is input to the signal input/output 504. The signal obtained by the signal input/output 504 is supplied to a signal processor 508. The signal processor 508 performs processing such as noise removal, filtering, amplification, and signal calculation. The signal processed by the signal processor 508 is supplied to a signal analyzer 510. The signal analyzer 510 extracts, for example, a specific signal for magnetoencephalography measurement. In the signal analyzer 510, for example, signal analysis for matching signal phases is performed.

The output of the signal analyzer 510 (data for which signal analysis has been completed) is supplied to a data processor 512. The data processor 512 performs data analysis. In this data analysis, for example, image data such as MRI (Magnetic Resonance Imaging) can be incorporated. In this data analysis, for example, scalp potential information such as EEG (Electroencephalogram) can be incorporated. For example, a data part 514 such as MRI or EEG is connected to the data processor 512. By the data analysis, for example, nerve ignition point analysis, inverse problem analysis, and the like are performed.

The result of the data analysis is supplied to, for example, an imaging diagnostic 516. Imaging is performed in the imaging diagnostic 516. Imaging assists in diagnosis.

The above series of operations is controlled by, for example, a control mechanism 502. For example, necessary data such as primary signal data or metadata in the middle of data processing is stored in the data server. The data server and the control mechanism may be integrated.

The diagnostic device 500 according to the embodiment includes the sensor 150 and the processor that processes an output signal obtained from the sensor 150. This processor includes, for example, at least one of a signal processor 508 and a data processor 512. The processor includes, for example, a computer.

In the sensor 150 shown in FIG. 16, the sensor part 301 is installed on the head of the human body. The sensor part 301 may be installed on the chest of the human body. This enables magnetocardiography measurement. For example, the sensor part 301 may be installed on the abdomen of a pregnant woman. This makes it possible to perform a fetal heartbeat test.

The sensor device including the subject is preferably installed in a shield room. Thereby, for example, the influence of geomagnetism or magnetic noise can be suppressed.

For example, a mechanism for locally shielding the measurement site of the human body or the sensor part 301 may be provided. For example, the sensor part 301 may be provided with a shield mechanism. For example, effective shielding may be performed in the signal analysis or the data processing.

In embodiments, the base body 302 may be flexible and may be substantially non-flexible. In the example shown in FIG. 17, the base body 302 is a continuous film processed into a hat shape. The base body 302 may be in a net shape. Thereby, for example, good wearability can be obtained. For example, the adhesion of the base body 302 to the human body is improved. The base body 302 may be helmet-shaped and may be rigid.

Figure 17:
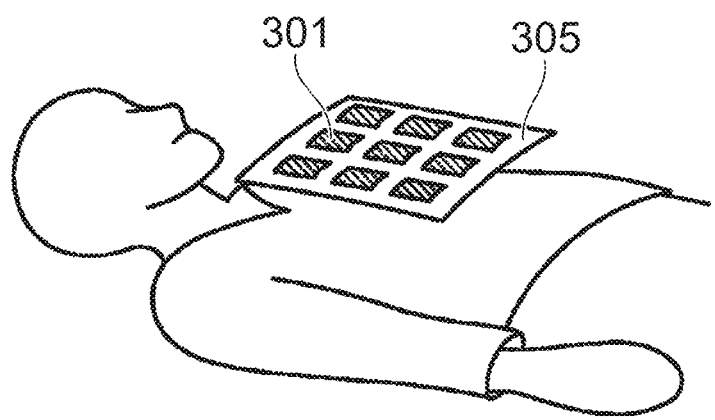
FIG. 17 is the inspection device according to the second embodiment.

FIG. 17 is a schematic view illustrating the inspection device according to the second embodiment.

FIG. 17 is an example of a magnetocardiograph. In the example shown in FIG. 17, the sensor part 301 is provided on a flat plate-shaped hard base body 305.

In the example shown in FIG. 17, the input/output of the signal obtained from the sensor part 301 is the same as the input/output described with respect to FIG. 16. In the example shown in FIG. 17, the processing of the signal obtained from the sensor part 301 is the same as the processing described with respect to FIG. 16.

There is a reference example of using a SQUID (Superconducting Quantum Interference Device) sensor as a device for measuring a weak magnetic field such as a magnetic field generated from a living body. In this reference example, since superconductivity is used, the device is large and the power consumption is also large. The burden on the measurement target (patient) is heavy.

According to the embodiment, the device can be downsized. Power consumption can be suppressed. The burden on the measurement object (patient) can be reduced. According to the embodiment, the SN ratio of magnetic field detection can be improved, Sensitivity can be improved.

The embodiment may include the following configurations (eg, technical proposals).

Configuration 1

A sensor, comprising:
an element part including a first element and a second element, each of the first element and the second element including a first magnetic element and a first conductive member; and
a control circuit part including
a first current circuit configured to supply a first current to the first conductive member, the first current including an AC component,
a differential circuit configured to output a differential signal corresponding to a difference of a first signal and a second signal, the first signal corresponding to a change in a first electrical resistance of the first magnetic element of the first element, the second signal corresponding to a change in a second electrical resistance of the first magnetic element of the second element, and
a phase detection circuit configured to perform a phase-detection of the differential signal with reference to the AC component,
the first electrical resistance changing in an even function with respect to the first current, the second electrical resistance changing in an even function with respect to the first current.

Configuration 2

The sensor according to Configuration 1, wherein
the first electrical resistance has a first value when a first value current is supplied to the first conductive member, a second value when a second value current is supplied to the first conductive member, and a third value when a third value current is supplied to the conductive member,
an orientation of the second value current is opposite to an orientation of the third value current,
an absolute value of the first value current is smaller than an absolute value of the second value current, and smaller than an absolute value of the third value current, and
the first value is lower than the second value and the third value, or higher than the second value and the third value.

Configuration 3

The sensor according to Configuration 1 or 2, wherein
the control circuit part further includes an element current circuit configured to supply an element current to the first magnetic element of each of the first element and the second element,
the first magnetic element includes one end part and an other end part, and the element current flows from the one end part to the other end part,
the first conductive member includes a first conductive member one part corresponding to the one end part and a first conductive member other part corresponding to the other end part, and
the first current has an orientation from the first conductive member one part to the first conductive member other part, or an orientation from the first conductive member other part to the first conductive member one part.

Configuration 4

The sensor according to Configuration 3, wherein
the first magnetic element includes
a first magnetic layer,
a first counter magnetic layer, and
a first non-magnetic layer provided between the first magnetic layer and the first counter magnetic layer,
a second direction from the first counter magnetic layer to the first magnetic layer crosses a first direction from one end part of the first magnetic element to an other end part of the first magnetic element.

Configuration 5

The sensor according to Configuration 4, wherein
a length of the first magnetic layer along the first direction is longer than a length of the first magnetic layer along a third direction, and the third direction crosses a plane including the first direction and the second direction.

Configuration 6

The sensor according to Configuration 5, wherein
the length of the first magnetic layer along the third direction is longer than the length of the first magnetic layer along the second direction, Configuration 7

The sensor according to Configuration 5 or 6, wherein the second element is separated from the first element in the third direction.

Configuration 8

The sensor according to any one of Configurations 4 o 7, wherein
the first non-magnetic layer includes at least one selected from the group consisting of Cu, Au and Ag.

Configuration 9

The sensor according to any one of Configurations 4 o 8, wherein
at least a part of the first conductive member overlaps the first magnetic element in the second direction.

Configuration 10

The sensor according to Configuration 1 or 2, wherein
each of the first element and the second element further includes
a second magnetic element and a second conductive member,
a first resistance element, and
a second resistance element, one end part of the first magnetic element is electrically connected to one end part of the first resistance element, one end part of the second magnetic element is electrically connected to an other end part of the first magnetic element, one end part of the second resistance element is electrically connected to an other end part of the first resistance element, an other end part of the second magnetic element is electrically connected to an other end part of the second resistance element, the first current circuit is configured to supply the first current to the second conductive member, the control circuit part further includes a detection circuit, the detection circuit is configured to detect a change in a first potential between the other end part of the first magnetic element of the first element and the other end part of the first resistance element of the first element as the first signal, and the detection circuit is configured to detect a change in a second potential between the other end part of the first magnetic element of the second element and the other end part of the first resistance element of the second element as the second signal.

Configuration 11

The sensor according to Configuration 10, wherein the control circuit part further includes an element current circuit, the element current circuit is configured to supply an element current between a connection point between the one end part of the first magnetic element of the first element and the one end part of the first resistance element of the first element, and a connection point between the other end part of the second magnetic element of the first element and the other end part of the second resistance element of the first element, and the element current circuit is configured to supply an element current between a connection point between the one end part of the first magnetic element of the second element and the one end part of the first resistance element of the second element, and a connection point between the other end part of the second magnetic element of the second element and the other end part of the second resistance element of the second element.

Configuration 12

The sensor according to Configuration 10 or 11, wherein the first conductive member includes a first conductive member one part corresponding to the one end part of the first magnetic element, and a first conductive member an other part corresponding to the other end part of the first magnetic element, the second conductive member includes a second conductive member one part corresponding to the one end part of the second magnetic element, and a second conductive member an other part corresponding to the other end part of the second magnetic element, and when the first current flows in an orientation from the first conductive member an other part to the first conductive member one part, the first current flows in an orientation from the second conductive member one part to the second conductive member an other part.

Configuration 13

The sensor according to Configuration 1 or 2, wherein each of the first element and the second element further includes a second magnetic element and a second conductive member, a third magnetic element and a third conductive member, and a fourth magnetic element and a fourth conductive member, one end part of the first magnetic element is electrically connected to one end part of the third magnetic element, one end part of the second magnetic element is electrically connected to an other end part of the first magnetic element, one end part of the fourth magnetic element is electrically connected to an other end part of the third magnetic element, an other end part of the second magnetic element is electrically connected to an other end part of the fourth magnetic element, the first current circuit is configured to supply the first current to the second conductive member, the third conductive member, and the fourth conductive member, the control circuit part further includes a detection circuit, the detection circuit is configured to detect a change in a first potential between the other end part of the first magnetic element of the first element and the other end part of the third magnetic element of the first element as the first signal, and the detection circuit is configured to detect a change in a second potential between the other end part of the first magnetic element of the second element and the other end part of the third magnetic element of the second element as the second signal, Configuration 14

The sensor according to Configuration 13, wherein the control circuit part further includes an element current circuit, the element current circuit is configured to supply an element current between a connection point between the one end part of the first magnetic element of the first element and the one end part of the third magnetic element of the first element, and a connection point between the other end part of the second magnetic element of the first element and the other end part of the fourth magnetic element of the first element, and the element current circuit is configured to supply an element current between a connection point between the one end part of the first magnetic element of the second element and the one end part of the third magnetic element of the second element, and a connection point between the other end part of the second magnetic element of the second element and the other end part of the fourth magnetic element of the second element.

Configuration 15

The sensor according to Configuration 13 or 14, wherein the first conductive member includes a first conductive member one part corresponding to the one end part of the first magnetic element and a first conductive member an other part corresponding to the other end part of the first magnetic element, the second conductive member includes a second conductive member one part corresponding to the one end part of the second magnetic element and a second conductive member an other part corresponding to the other end part of the second magnetic element, the third conductive member includes a third conductive member one part corresponding to the one end part of the third magnetic element and a third conductive member an other part corresponding to the other end part of the third magnetic element, the fourth conductive member includes a fourth conductive member one part corresponding to the one end part of the fourth magnetic element and a fourth conductive member an other part corresponding to the other end part of the fourth magnetic element, when the first current flows in an orientation from the first conductive member an other part to the first conductive member one part, the first current flows in an orientation from the second conductive member one part to the second conductive member an other part, the first current flows in an orientation from the third conductive member one part to the third conductive member an other part, and the first current flows in an orientation from the fourth conductive member an other part to the fourth conductive member one part, Configuration 16

The sensor according to any one of Configurations 1 to 15, wherein at least a part of the differential circuit is included in an analogue circuit, and at least a part of the phase detection circuit is included in FPGA.

Configuration 17

The sensor according to Configurations 16, wherein at least a part of the first current circuit is included in the FPGA.

Configuration 18

The sensor according to Configuration 16 or 17, wherein the FPGA is configured to process an output signal of the phase detection circuit.

Configuration 19

The sensor according to any one of Configurations 1 to 15, comprising:

a plurality of the element parts, the control circuit part includes a plurality of the differential circuits corresponding to the plurality of element parts, and a plurality of the phase detection circuits corresponding to the plurality of differential circuits, at least a part of each of the plurality of differential circuits is included in an analogue circuit, the plurality of phase detection circuits are included in FPGA, the FPGA is configured to process an output signal of each of the plurality of phase detection circuits, and the FPGA is configured to control the plurality of phase detection circuits.

Configuration 20

An inspection device, comprising:

the sensor according to any one of Configurations 1 to 19; and a processor configured to process a signal output from the sensor.

According to the embodiment, a sensor and an inspection device can be provided, in which characteristics are possible to be improved.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as element parts, conductive members, control circuit parts, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, and inspection devices practicable by an appropriate design modification by one skilled in the art based on the sensors, and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
an element part including a first element and a second element, each of the first element and the second element including a first magnetic element and a first conductive member; and
a control circuit part including
a first current circuit configured to supply a first current to the first conductive member, the first current including an AC component,
a differential circuit configured to output a differential signal corresponding to a difference of a first signal and a second signal, the first signal corresponding to a change in a first electrical resistance of the first magnetic element of the first element, the second signal corresponding to a change in a second electrical resistance of the first magnetic element of the second element, and
a phase detection circuit configured to perform a phase detection of the differential signal with reference to the AC component,
the first electrical resistance changing in an even function with respect to the first current, the second electrical resistance changing in an even function with respect to the first current.

2. The sensor according to claim 1, wherein
the first electrical resistance has a first value when a first value current is supplied to the first conductive member, a second value when a second value current is supplied to the first conductive member, and a third value when a third value current is supplied to the conductive member,
an orientation of the second value current is opposite to an orientation of the third value current,
an absolute value of the first value current is smaller than an absolute value of the second value current, and smaller than an absolute value of the third value current, and
the first value is lower than the second value and the third value, or higher than the second value and the third value.

3. The sensor according to claim 1, wherein
the control circuit part further includes an element current circuit configured to supply an element current to the first magnetic element of each of the first element and the second element,
the first magnetic element includes one end part and an other end part, and the element current flows from the one end part to the other end part,
the first conductive member includes a first conductive member one part corresponding to the one end part and a first conductive member other part corresponding to the other end part, and
the first current has an orientation from the first conductive member one part to the first conductive member other part, or an orientation from the first conductive member other part to the first conductive member one part.

4. The sensor according to claim 3, wherein
the first magnetic element includes
a first magnetic layer,
a first counter magnetic layer, and
a first non-magnetic layer provided between the first magnetic layer and the first counter magnetic layer,
a second direction from the first counter magnetic layer to the first magnetic layer crosses a first direction from one end part of the first magnetic element to an other end part of the first magnetic element.

5. The sensor according to claim 4, wherein
a length of the first magnetic layer along the first direction is longer than a length of the first magnetic layer along a third direction, and the third direction crosses a plane including the first direction and the second direction.

6. The sensor according to claim 5, wherein
the length of the first magnetic layer along the third direction is longer than the length of the first magnetic layer along the second direction.

7. The sensor according to claim 5, wherein
the second element is separated from the first element in the third direction.

8. The sensor according to claim 4, wherein
the first non-magnetic layer includes at least one selected from the group consisting of Cu, Au and Ag.

9. The sensor according to claim 4, wherein
at least a part of the first conductive member overlaps the first magnetic element in the second direction.

10. The sensor according to claim 1, wherein
each of the first element and the second element further includes
a second magnetic element and a second conductive member,
a first resistance element, and
a second resistance element,
one end part of the first magnetic element is electrically connected to one end part of the first resistance element,
one end part of the second magnetic element is electrically connected to an other end part of the first magnetic element,
one end part of the second resistance element is electrically connected to an other end part of the first resistance element,
an other end part of the second magnetic element is electrically connected to an other end part of the second resistance element,
the first current circuit is configured to supply the first current to the second conductive member,
the control circuit part further includes a detection circuit,
the detection circuit is configured to detect a change in a first potential between the other end part of the first magnetic element of the first element and the other end part of the first resistance element of the first element as the first signal, and
the detection circuit is configured to detect a change in a second potential between the other end part of the first magnetic element of the second element and the other end part of the first resistance element of the second element as the second signal.

11. The sensor according to claim 10, wherein
the control circuit part further includes an element current circuit,
the element current circuit is configured to supply an element current between a connection point between the one end part of the first magnetic element of the first element and the one end part of the first resistance element of the first element, and a connection point between the other end part of the second magnetic element of the first element and the other end part of the second resistance element of the first element, and
the element current circuit is configured to supply an element current between a connection point between the one end part of the first magnetic element of the second element and the one end part of the first resistance element of the second element, and a connection point between the other end part of the second magnetic element of the second element and the other end part of the second resistance element of the second element.

12. The sensor according to claim 10, wherein
the first conductive member includes a first conductive member one part corresponding to the one end part of the first magnetic element, and a first conductive member an other part corresponding to the other end part of the first magnetic element,
the second conductive member includes a second conductive member one part corresponding to the one end part of the second magnetic element, and a second conductive member an other part corresponding to the other end part of the second magnetic element, and
when the first current flows in an orientation from the first conductive member an other part to the first conductive member one part, the first current flows in an orientation from the second conductive member one part to the second conductive member an other part.

13. The sensor according to claim 1, wherein
each of the first element and the second element further includes
a second magnetic element and a second conductive member,
a third magnetic element and a third conductive member, and
a fourth magnetic element and a fourth conductive member,
one end part of the first magnetic element is electrically connected to one end part of the third magnetic element,
one end part of the second magnetic element is electrically connected to an other end part of the first magnetic element,
one end part of the fourth magnetic element is electrically connected to an other end part of the third magnetic element,
an other end part of the second magnetic element is electrically connected to an other end part of the fourth magnetic element, the first current circuit is configured to supply the first current to the second conductive member, the third conductive member, and the fourth conductive member, the control circuit part further includes a detection circuit, the detection circuit is configured to detect a change in a first potential between the other end part of the first magnetic element of the first element and the other end part of the third magnetic element of the first element as the first signal, and the detection circuit is configured to detect a change in a second potential between the other end part of the first magnetic element of the second element and the other end part of the third magnetic element of the second element as the second signal.

14. The sensor according to claim 13, wherein the control circuit part further includes an element current circuit, the element current circuit is configured to supply an element current between a connection point between the one end part of the first magnetic element of the first element and the one end part of the third magnetic element of the first element, and a connection point between the other end part of the second magnetic element of the first element and the other end part of the fourth magnetic element of the first element, and the element current circuit is configured to supply an element current between a connection point between the one end part of the first magnetic element of the second element and the one end part of the third magnetic element of the second element, and a connection point between the other end part of the second magnetic element of the second element and the other end part of the fourth magnetic element of the second element.

15. The sensor according to claim 13, wherein the first conductive member includes a first conductive member one part corresponding to the one end part of the first magnetic element and a first conductive member an other part corresponding to the other end part of the first magnetic element, the second conductive member includes a second conductive member one part corresponding to the one end part of the second magnetic element and a second conductive member an other part corresponding to the other end part of the second magnetic element, the third conductive member includes a third conductive member one part corresponding to the one end part of the third magnetic element and a third conductive member an other part corresponding to the other end part of the third magnetic element, the fourth conductive member includes a fourth conductive member one part corresponding to the one end part of the fourth magnetic element and a fourth conductive member an other part corresponding to the other end part of the fourth magnetic element, when the first current flows in an orientation from the first conductive member an other part to the first conductive member one part, the first current flows in an orientation from the second conductive member one part to the second conductive member an other part, the first current flows in an orientation from the third conductive member one part to the third conductive member an other part, and the first current flows in an orientation from the fourth conductive member an other part to the fourth conductive member one part.

16. The sensor according to claim 1, wherein at least a part of the differential circuit is included in an analogue circuit, and at least a part of the phase detection circuit is included in FPGA.

17. The sensor according to claim 16, wherein at least a part of the first current circuit is included in the FPGA.

18. The sensor according to claim 16, wherein the FPGA is configured to process an output signal of the phase detection circuit.

19. The sensor according to claim 1, comprising:

a plurality of the element parts, the control circuit part includes a plurality of the differential circuits corresponding to the element parts, and a plurality of the phase detection circuits corresponding to the differential circuits, at least a part of each of the differential circuits is included in an analogue circuit, the phase detection circuits are included in FPGA, the FPGA is configured to process an output signal of each of the phase detection circuits, and the FPGA is configured to control the phase detection circuits.

20. An inspection device, comprising:

the sensor according to claim 1; and a processor configured to process a signal output from the sensor.

* * * * *